(12) United States Patent
Pfaff et al.

(10) Patent No.: US 6,656,259 B2
(45) Date of Patent: Dec. 2, 2003

(54) MULTILAYERED INTERFERENCE PIGMENTS

(75) Inventors: Gerhard Pfaff, Münster (DE); Helge Kniess, Weiterstadt (DE); Peter Reynders, Griesheim (DE)

(73) Assignee: Merck Patent Gesellschaft mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 10/210,873

(22) Filed: Aug. 2, 2002

(65) Prior Publication Data

US 2003/0039836 A1 Feb. 27, 2003

(30) Foreign Application Priority Data

Aug. 2, 2001 (DE) .......................................... 101 37 831

(51) Int. Cl.$^7$ .............................................. C04B 14/00
(52) U.S. Cl. ...................... 106/415; 106/430; 106/431; 106/435; 106/436; 106/426; 106/446
(58) Field of Search .................................. 106/415, 430, 106/431, 435, 436, 426, 446

(56) References Cited

U.S. PATENT DOCUMENTS 6,132,873 A * 10/2000 Dietz et al. ................. 428/404

FOREIGN PATENT DOCUMENTS

| JP | 2000-239559 | * | 9/2000 |
| WO | WO93/08237 | | 4/1993 |

* cited by examiner

*Primary Examiner*—C. Melissa Koslow
*Assistant Examiner*—Shalie Manlove
(74) *Attorney, Agent, or Firm*—Millen, White, Zelano & Branigan, P.C..

(57) ABSTRACT

The invention relates to multilayered interference pigments which comprise a platelet-shaped substrate of silicon dioxide which is coated alternately with layers of light-transparent materials having refractive indices of n>1.8 and layers of light-transparent materials having refractive indices of n≦1.8, where the optical thickness of the platelet-shaped substrate and the optical thickness of the individual layers of light-transparent materials having refractive indices of n≦1.8 are the same.

15 Claims, 21 Drawing Sheets

Example 1

Comparative Example 1

Example 2

Comparative Example 2

Example 3

Comparative Example 3

Example 4

Steep viewing angle: L 84.89; a 14.96; b 93.08
Flat viewing angle: L 73.51; a -69.0; b -1.80

Comparative Example 4

Steep viewing angle: L 75.02; a 0.20; b 70.81
Flat viewing angle: L 67.62; a -42.58; b 5.65

Example 5

Steep viewing angle: L 53.68; a 82.51; b -59.45
Flat viewing angle: L 92.28; a -41.61; b 96.49

Comparative Example 5

Steep viewing angle: L 58.77; a 60.11; b -31.66
Flat viewing angle: L 80.33; a -28.97; b 41.26

Example 6

Comparative Example 6

Steep viewing angle: L 77.21; a -33.34; b 10.36
Flat viewing angle: L 41.60; a 41.17; b -63.88

Fig. 19 Gold-green/violet

Copmparative Example 7'

MULTILAYERED INTERFERENCE PIGMENTS

The invention relates to multilayered interference pigments which comprise a platelet-shaped substrate of silicon dioxide which is coated alternately with layers of light-transparent materials having refractive indices of n>1.8 and layers of light-transparent materials having refractive indices of n≦1.8, where the optical thickness of the platelet-shaped substrate and the optical thickness of the individual layers of light-transparent materials having refractive indices of n≦1.8 are the same, and to a process for the preparation of these pigments and to their use.

The use of luster or effect pigments which exhibit interference phenomena is widespread. In automobile paints, decorative coatings of all types and in the coloring of plastics, paints and printing inks, in particular inks for security printing, and in applications in decorative cosmetics, pigments of this type have become indispensable.

In the matrix surrounding them, these pigments ideally line up parallel to the surface of the coating and develop their optical action through a complex interaction of interference, reflection and absorption of the incident light. Bright coloring, changing between various colors depending on the viewing angle, so-called color flops, or varying brightness impressions are of central interest for the various applications.

Pigments of this type are generally prepared by coating platelet-shaped metallic or non-metallic substrates with metal oxide or metal layers. Recent years have seen increased development of pigments which have a multilayered structure on the platelet-shaped support. This enables, in particular, color flops in which the human eye perceives different hues depending on the viewing angle to be set specifically. Most of these pigments are based on platelet-shaped substrates of metals or synthetic or natural phyllosilicates, such as mica, talc or glass.

The phyllosilicates have, in particular, the disadvantage that the thickness of the substrate varies in a broad range and cannot be set specifically, which results, even in the case of transparent substrates, in light transmission and reflection at the substrate proceeding in a substantially uncontrollable manner and therefore not being utilizable in a specific manner.

However, interference pigments with substrates of silicon dioxide are also known. Thus, for example, DE 41 37 764 describes pigments based on silicon dioxide particles which have been coated with iron oxide, where the iron oxide proportion, based on the silicon dioxide particles, is greater than 350% by weight. Pigments of this type have good hiding power, intense hues and a color flop although they are not based on platelet-shaped substrates. The color flop here becomes more pronounced with increasing iron oxide proportion. For pigment applications in which a color flop is desired, very thick iron oxide layers therefore have to be applied. Due to the iron oxide coating, pigments prepared in this way only allow a limited range of hues and are only of limited applicability in preparations in which transparency and thin layer thicknesses are necessary. In addition, a large proportion of the incident light cannot be reflected in an optimum manner since the pigments cannot align parallel to the surface in coatings.

EP 0 608 388 discloses a platelet-shaped pigment which can consist, inter alia, of a silicon dioxide matrix which has been coated with one or more layers of thin, transparent or semi-transparent reflective layers of metal oxides or metals. The matrix here is preferably colored by addition of various colorants. Pigments of high color purity and high tinting strength whose hiding power is determined by the degree of coloring of the matrix are obtained. The thickness of the matrix here can be set in a broad range. This specification does not describe any pigments which have more than one optically active layer on the substrate. These pigments therefore have the action of a pigment having a total of three optically active layers.

DE 196 14 637 discloses goniochromatic luster pigments based on silicon dioxide platelets to which a black, at least partially transparent layer (A) and optionally an outer layer (B) which consists of a colorless or selectively absorbent metal oxide and/or contains phosphate, chromate and/or vanadate has been applied by means of a CVD process.

Layer (A) here, with a thickness of from 1 to 50 nm, preferably consists of metals and/or non-selectively absorbent metal compounds. Layer (B) can consist of high- or low-refractive-index metal oxides.

Due to the black layer (A), these pigments exhibit intense interference colors and striking hue changes depending on the viewing angle. However, metal and metal oxide layers here are applied by gas-phase decomposition of, in particular, organometallic compounds, which makes the preparation process too complex and expensive for mass production of pigments and means that it is associated with major safety precautions.

DE 196 18 569 relates to multilayered interference pigments comprising a transparent support material which is coated with alternating layers of a metal oxide of low refractive index and of a metal oxide of high refractive index.

The transparent support material here can consist of $SiO_2$ platelets. In one example, $TiO_2$, $SiO_2$ and $TiO_2$ are applied alternately to an $SiO_2$ platelet, with the individual layer thicknesses being very different. In these pigments, the interference hue on perpendicular viewing and the number and hues of the colors passed through depending on the viewing angle (color flop) and the chroma (tinting strength) of the pigment only become visible when the final pigment structure has been achieved. In this case, however, color corrections are only perceptible in the outer layer. This can generally only be achieved by application of relatively thick layers, which is economically unfavorable and in extreme cases can result in the product no longer being usable for certain applications merely owing to the greater layer thicknesses.

The chroma of such pigments also varies greatly in the various colors of a color flop, i.e. the various colors are perceived with different intensity and do not have pronounced brightness.

There was therefore a demand for multilayered interference pigments which exhibit intense interference colors and strong angle dependence of the interference color, and for a simple and inexpensive preparation process by means of which the color properties of the end product are definitively determined as early as the first process step.

The object of the invention is therefore to provide further multilayered interference pigments based on silicon dioxide platelets which have a strong angle dependence of the interference colors, with all the hues passed through during a change in the viewing angle having intense chroma and excellent brightness.

A further object of the invention was to provide a process for the preparation of multilayered interference pigments in which the various interference hues to be passed through at different viewing angles can be set definitively as early as the first coating of the substrate.

An additional object of the invention was to indicate uses for the pigments according to the invention.

The object of the invention is achieved by a multilayered interference pigment which comprises a substrate of platelet-shaped silicon dioxide which is coated alternately with two or more layers of light-transparent materials having refractive indices of n>1.8 and therebetween one or more layers of light-transparent materials having refractive indices of n≦1.8, where the optical thickness of the platelet-shaped substrate and the optical thickness of the individual layers of light-transparent materials having refractive indices of n≦1.8 are substantially the same.

The object of the invention is likewise achieved by a process for the preparation of a multilayered interference pigment in which a platelet-shaped substrate of silicon dioxide is suspended in water and coated alternately a number of times with a metal oxide hydrate or BiOCl having a refractive index of n>1.8 and a metal oxide hydrate or metal fluoride having a refractive index of n≦1.8 by addition and precipitation of the corresponding inorganic metal compounds, where the pH necessary for precipitation of the respective metal oxide hydrate, BiOCl or metal fluoride is set and kept constant by simultaneous addition of acid or base, and the coated substrate is subsequently separated off from the aqueous suspension, dried and, if desired, calcined, and where an optical layer thickness in the case of the individual layers of a metal oxide hydrate or metal fluoride having a refractive index of n≦1.8 to be applied to the substrate is set in such a way that it is equal to the optical layer thickness of the platelet-shaped substrate after drying and any calcination.

The object of the invention is furthermore achieved by the use of the above-described multilayered interference pigments according to the invention for the pigmenting of paints, coatings, printing inks, plastics, cosmetic formulations, glasses, paper, films, packaging materials, ceramic materials, for laser marking, in security applications and in dry preparations and pigment preparations.

The substrate of the interference pigment according to the invention consists of platelet-shaped silicon dioxide particles which have a uniform layer thickness and are preferably produced in accordance with international application WO 93/08237 on a continuous belt by solidification and hydrolysis of a water-glass solution. The term "uniform layer thickness" here is taken to mean a layer thickness tolerance of from 3 to 10%, preferably from 3 to 5%, of the total dry layer thickness of the particles. The platelet-shaped silicon dioxide particles are generally in amorphous form.

The diameter of the $SiO_2$ platelets is usually between 1 and 250 µm, preferably between 2 and 100 µm. Their thickness is between 100 and 600 nm, preferably from 200 to 500 nm and particularly preferably from 200 to 375 nm.

The mean aspect ratio of the platelet-shaped $SiO_2$ particles, i.e. the ratio of the mean length measurement, which corresponds to the mean diameter here, to the mean thickness measurement, is usually from 5 to 200, preferably from 20 to 150 and particularly preferably from 30 to 120.

Suitable light-transparent materials having refractive indices of n≦1.8 are metal oxides, metal fluorides or metal oxide hydrates, which are preferably colorless, such as, for example, $SiO_2$, $SiO(OH)_2$, $Al_2O_3$, $AlO(OH)$, $B_2O_3$, $MgF_2$ or mixtures thereof.

Particular preference is given to $SiO_2$.

The thickness of the individual layers of these materials is between 100 and 600 nm, preferably from 200 to 500 nm and particularly preferably from 200 to 375 nm for $SiO_2$ layers and from 50 to 600 nm, preferably from 80 to 400 nm and particularly preferably from 100 to 350 nm for the other materials.

The thickness of the layers here is set in such a way that the optical layer thickness of the substrate is substantially equal to the optical layer thickness of each individual layer of light-transparent materials having refractive indices of n≦1.8. The term "substantially the same optical layer thickness" here is taken to mean that the deviation between the optical layer thickness of the substrate and the optical layer thickness of each individual layer of light-transparent materials having refractive indices of n≦1.8 is at most 5%, but is preferably at most 3%, based on the optical layer thickness of the substrate. The optical layer thickness of the individual layers is determined from the product of the refractive index n of the layer material and the actual (physically measurable) layer thickness d. If the material having a refractive index of n≦1.8 is silicon dioxide, the actual thickness of the substrate is equal to the actual thickness of the individual layers of silicon dioxide. However, if the material having a refractive index of n≦1.8 is $SiO(OH)_2$, $Al_2O_3$, $AlO(OH)$, $B_2O_3$, $MgF_2$ or a mixture of two or more of these or a mixture with $SiO_2$ or another light-transparent material having a refractive index of n≦1.8, the actual layer thickness of this layer is set in such a way that its optical layer thickness corresponds to the optical layer thickness of the substrate. This is a layer thickness of 500 nm and a refractive index of 1.5 (SiO2), the optical thickness is 750 nm. For a substrate having such an optical layer thickness, the low refractive layer(s) should have an optical layer thickness of no less than 12.5 and no more than 787.5.

For this reason, the actual layer thicknesses of the individual layers of light-transparent materials having refractive indices of n≦1.8 are subject to certain variations, which also applies to the ratio of the actual layer thicknesses of these individual layers to the actual layer thickness of the substrate. Thus, for the representative layers disclosed, the actual layer thicknesses of the individual layers of light-transparent materials having refractive indices of n≦1.8 may be subject to variations which are less than or equal to 20%, based on the actual layer thickness of the substrate, but preferably from about 10 to 20%.

The ratio of the layer thickness of each individual layer of materials having refractive indices of n≦1.8 to the layer thickness of the substrate is therefore greater than or equal to 0.8 and less than or equal to 1.2. All individual layers of light-transparent materials having refractive indices of n≦1.8 preferably consist of the same material. However, the composition of the layers may also be different from layer to layer or layers of two or more different materials may alternate in a constant sequence. In a particularly preferred embodiment, both the substrate and the individual layers of light-transparent materials having refractive indices of n≦1.8 consist of silicon dioxide.

One or more such layers, in particular from one to three layers and particularly preferably one layer, are located on each face of the the substrate. Light-transparent materials having refractive indices of n>1.8 which can be employed are metal oxides which are known for pigment applications, in particular colorless metal oxides, such as $TiO_2$, $ZrO_2$, $ZnO$ or $SnO_2$, mixtures thereof or alternatively BiOCl.

Particular preference is given to $TiO_2$.

The thickness of these layers is in each case from about 20 to 300 nm and preferably from 30 to 200 nm.

The thickness of the individual layers of light-transparent materials having refractive indices of n>1.8 here is always smaller than the thickness of the individual layers of light-transparent materials having refractive indices of n≦1.8 or the thickness of the substrate.

The multilayered pigment according to the invention comprises two or more layers of materials having refractive indices of n>1.8, but preferably two layers. These layers may consist of identical or different materials and have identical or different layer thicknesses.

These layers preferably consist of the same materials and have identical layer thicknesses. This is particularly the case if the layer thicknesses of the substrate, the first layer of a light-transparent material having a refractive index of n>1.8 and the layer thickness of the first layer of a light-transparent material having a refractive index of $\leq 1.8$ have been matched to one another in such a way that the incident light of certain wavelengths is amplified to the same extent by each layer, i.e. the optical layer thicknesses satisfy the relationship $(2n+1) \lambda/4$, where $n=0,1,2,3\ldots$ and $\lambda$ denotes the mean wavelength of the incident light. In this case, the term constructive interference is used. It is preferred that destructive interference, i.e. maximum attenuation of the interference, which occurs at optical layer thicknesses which satisfy the relationship $n \lambda/2$, is avoided.

However, applications in which this known principle of optimum color setting has to be deviated from may also occur. Thus, the color and luster effect of an interference pigment is to a high degree determined by the medium in which the pigment is employed. The same pigment as, for example, a pigment powder in air exhibits different color properties than in a binder matrix of a coating solution. For this reason, interference pigments are customized individually for their later area of application.

If the multilayered interference pigment according to the invention is intended to be employed in a medium whose refractive index is different from the refractive indices of the individual layers of the pigment, the layer thicknesses of the individual layers of light-transparent material having a refractive index of n>1.8 will, where appropriate, have to differ from one another for optimum color setting. This deviation can be up to 50%, based on the layer thickness of the layer having a refractive index >1.8 applied first, and can easily be determined by means of expert optimization work requiring no inventive step.

Equally, matching can be carried out if intermediate hues or particularly steep edges of the reflection bands of the pigment are desired for certain areas of application.

However, the best results can be achieved with pigments in accordance with the present invention which have a completely symmetrical layer structure. In this case, the individual layers of a light-transparent material having a refractive index of $\leq 1.8$ consist of the same material and have the same layer thicknesses. Likewise, the individual layers of a light-transparent material having a refractive index of n>1.8 have the same layer thicknesses and consist of the same material. It is particularly preferred here for the substrate and the layers of a light-transparent material having a refractive index of $\leq 1.8$ not only to have the same optical layer thicknesses, but likewise to consist of the same material, namely $SiO_2$, and for the individual layers of a light-transparent material having a refractive index of n>1.8 to consist of $TiO_2$.

In the latter case, a symmetrical pigment having the layer structure
$TiO_2$—$SiO_2$—$TiO_2$—$SiO_2$—$TiO_2$—$SiO_2$(-substrate)-$TiO_2$—$SiO_2$—$TiO_2$—$SiO_2$—$TiO_2$,
which represents a pigment having eleven optically active layers, although the substrate has only been coated 5 times, is obtained. By subsequent coating with a further layer of $TiO_2$ and a further layer of $SiO_2$, the layer sequence can be extended as desired. All layers of the same material here also have the same layer thicknesses. The number of layers here is restricted by the achievable color effects and the requisite effort. In general, the layer structure described above is sufficient to obtain pigments having clear and bright interference colors, strong dependence of the interference colors on the viewing angle and a uniform chroma (color depth) for all interference colors passed through as a function of the angle.

Surprisingly, it has been found that merely the layer structure
$TiO_2$—$SiO_2$—$TiO_2$—$SiO_2$(-substrate)—-$TiO_2$—$SiO_2$—$TiO_2$
results in extremely good pigments having the properties described above, where a pigment having seven optically active layers has been obtained by coating the substrate with only three layers.

Of particular interest and very surprising was the fact that this pigment exhibits a color flop which is exhibited even by the pigment of the composition
$TiO_2$—$SiO_2$(-substrate)—-$TiO_2$
which has only three optically active layers whose actual individual layer thicknesses are in each case identical with the individual layer thicknesses of the substrate and of the first coating of the pigments with seven or eleven optically active layers. The range of the color flop visible in the Hunter L,a,b color system may be slightly wider with a greater number of layers, but the same hues are observed, depending on the viewing angle, as in the three-layer pigment with the same layer thicknesses. Due to the additional coating with further layers of the same composition and layer thickness, however, the chroma of the pigments can be noticeably changed, i.e. increased, for each hue passed through depending on the viewing angle. The color brightness in the multilayered interference pigments according to the invention is also significantly more pronounced than in the corresponding three-layer pigments.

The above-said naturally also applies to the pigments according to the invention which are not composed exclusively of $SiO_2$ and $TiO_2$, but instead comprise one or more of the other materials described as suitable above in the individual layers and have a symmetrical structure which is within the above-described limits with respect to the layer thicknesses and layer-thickness tolerances.

The process according to the invention for the preparation of a multilayered interference pigment is preferably a wet-chemical process in which the known wet-chemical coating technologies developed for the preparation of pearlescent pigments can be used and which are described, for example, in the following publications:
DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017.

For the coating, the platelet-shaped substrate of silicon dioxide is suspended in water and coated alternately a number of times with a metal oxide hydrate of a metal oxide or BiOCl, which in each case having a refractive index of n>1.8 and a metal oxide hydrate of a metal oxide or metal fluoride, which have a refractive index of $n\leq 1.8$ by addition and precipitation of the corresponding inorganic metal compounds, where the pH necessary for precipitation of the respective metal oxide hydrate, BiOCl or metal fluoride is set and kept constant by simultaneous addition of acid or base, and the coated substrate is subsequently separated off from the aqueous suspension, dried and, if desired, calcined, and where an optical layer thickness in the case of the individual layers of a metal oxide hydrate of a metal oxide or metal fluoride, which have a refractive index of $n\leq 1.8$ to be applied to the substrate is set in such a way that it is equal to the optical layer thickness of the platelet-shaped substrate after drying and any calcination.

The calcination temperature here can be optimized with respect to the coating present in each case. In general, however, the calcination temperature is between 250 and 1000° C., in particular between 350 and 900° C. The pigments can also be separated off, dried and, if desired, calcined after application of each individual layer before they are re-dispersed for application of the next layer.

If the material having a refractive index of n>1.8 is $TiO_2$, the process described in U.S. Pat. No. 3,553,001 is preferably employed for application of these layers.

In this process, an aqueous solution of an inorganic titanium salt is slowly added to a suspension, heated to about 50–100° C., in particular 70–80° C., of the platelet-shaped, optionally pre-coated silicon dioxide particles, and the pH is kept substantially constant at from 0.5 to 5, in particular from about 1.5 to 2.5, by simultaneous metering-in of a base. As soon as the desired layer thickness of the $TiO_2$ oxide hydrate has been reached, the addition of the titanium salt solution and the base is stopped.

This process is also known as the titration process and has the special feature that an excess of titanium salt is not present, but instead only such an amount as is necessary for uniform coating with the hydrated $TiO_2$ and also can be taken up by the surface of the $SiO_2$ substrate to be coated is always provided per time unit. The solution therefore contains no-hydrated titanium dioxide particles which are not deposited on the surface to be coated.

If the light-transparent material having a refractive index of $n \leq 1.8$ is silicon dioxide, the following process is used for application of the corresponding layer or layers:

A sodium water-glass solution is added to a suspension, heated to about 50 to 100° C., in particular 70 to 80° C., of the substrate which has already been coated one or more times. At the same time, the pH is kept constant at from 4 to 10, preferably from 6.5 to 8.5, by addition of 10% hydrochloric acid. When the addition of the water-glass solution is complete, the mixture is stirred for a further approximately 30 minutes.

In principle, CVD or PVD processes for the coating of particles are also suitable for the preparation of the pigments according to the invention. It is necessary here that the substrate is kept in uniform motion during the vapor-deposition operation so as to ensure homogeneous coating of all particle surfaces.

If in addition further layers of organic or inorganic colored pigments, such as colored metal oxides, for example goethite, magnetite, haematite, chromium oxide, titanium suboxides and chromium/iron mixed oxides, or colored pigments, such as Berlin Blue, Turnbull's Blue, bismuth vanadate, chromium hydroxide, cobalt aluminate, ultramarine, Tenard's Blue, cadmium sulfides or selenides, chromate pigments or carbon black, but also organic colored pigments, such as indigo, thioindigo and derivatives thereof, azo pigments, phthalocyanines, benzimidazoles, anthraquinones, indanthrene dyes, perinones, quinacridones, metal chalcogenides, metal chalcogenide hydrates or Carmine Red, are applied to the upper layer of metal oxide or BiOCl having a refractive index of n>1.8 on the pigments according to the invention, the powder color of the pigments can be significantly changed, enabling further interesting color effects to be achieved.

These layers are applied by known processes, as described, for example, in EP 0 141 173, EP 0 332 071, DE 19 51 696, DE 19 51 697, DE 23 13 332 and DE 40 09 567.

The finished pigment may also be subjected to aftertreatment or after-coating in order to increase its light, weather or chemical stability or in order to simplify handling of the pigment, in particular with respect to incorporation into various media. Aftercoating or aftertreatment processes are disclosed, for example, in DE 22 15 191, DE 31 51 354, DE 32 35 017, DE 33 34 598, DE 40 30 727, EP 0 649 886, WO 97/29059, WO 99/57204 and U.S. Pat. No. 5,759,255.

The substances applied here merely make up a proportion by weight of from 0.1 to 5% by weight, preferably from 0.5 to 3% by weight, of the pigment as a whole.

The pigments according to the invention can be employed in a conventional manner for pigmenting paints, laquers, printing inks, plastics, cosmetic formulations, ceramic materials, paper and glasses and in various security applications. The pigments according to the invention are furthermore also suitable for laser marking of paper and plastics, for applications in the agricultural sector, and for the preparation of pigment preparations and dry preparations, such as, for example, pellets, granules, chips, etc., which are preferably used in printing inks and surface coatings. They can likewise be employed in a multiplicity of known binders used in paint systems and can be used both in aqueous systems and in solvent-based systems.

The pigments of the present invention can of course advantageously also be mixed with organic dyes, organic pigments and other inorganic single- or multilayered pigments of all types, such as, for example, the conventional pearlescent pigments based on phyllosilicates, glass, $SiO_2$ or metal substrates, and also with holographic pigments LCPs (liquid crystal polymers) and can be used together therewith. Mixing with conventional binders and fillers in any ratio is also possible.

The multilayered interference pigments according to the invention are distinguished by a strong angle dependence of the interference colors, with all hues which can be observed as a function of the illumination or viewing angle having intense chroma and excellent color brightness. They can be prepared without particular safety measures by means of a simple and inexpensive process in which the colors which the finished pigment is to have can be established as early as the first process step.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure[s] of all applications, patents and publications, cited above or below, and of corresponding Germany Application No. 10137831.9, filed Aug. 2, 2001, is hereby incorporated by reference.

BRIEF DESCRIPTION OF THE DRAWINGS

The FIGS. 1–21 detail the optical properties of materials produced in the Examples.

EXAMPLES

Example 1

Figure 1:
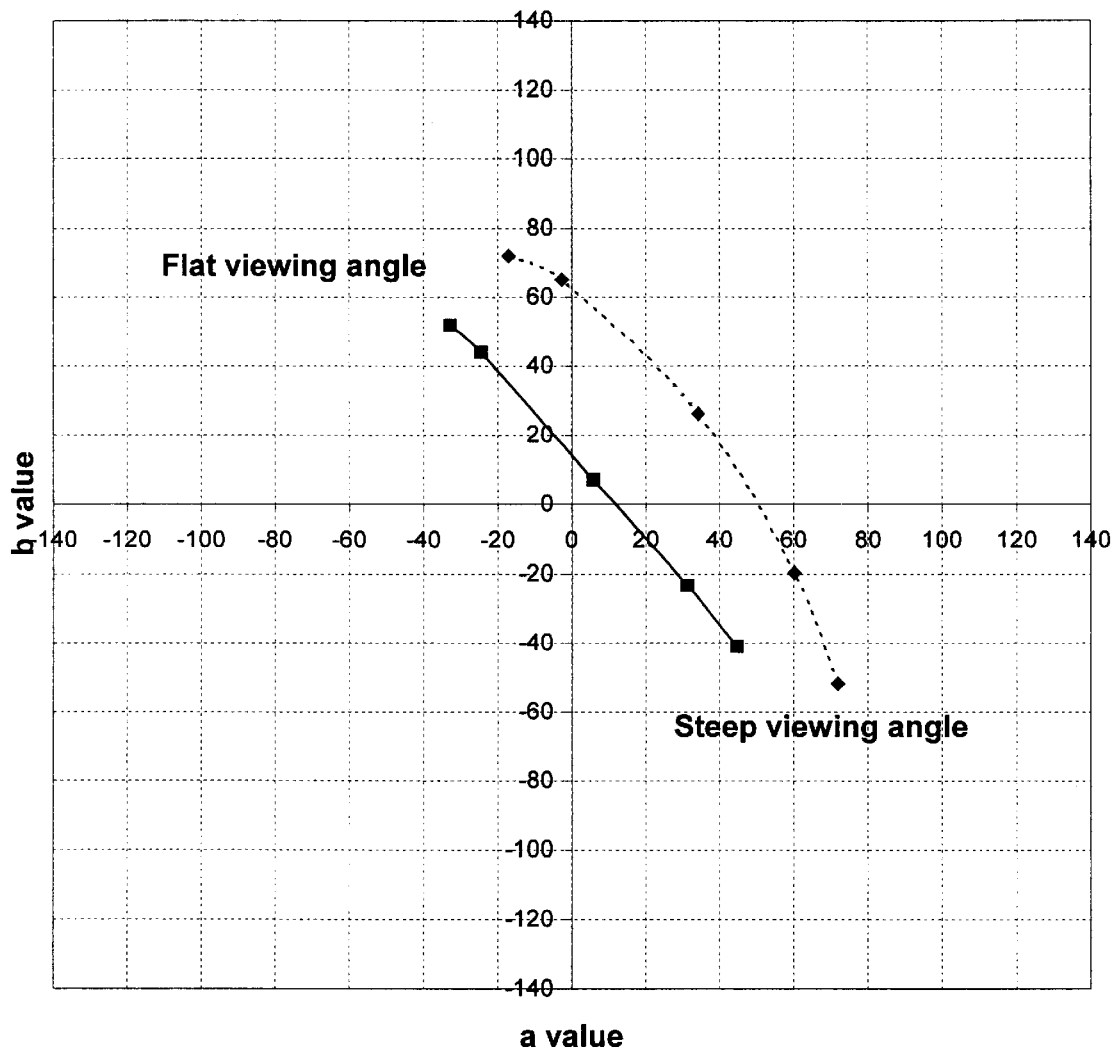

Preparation of a pigment having the composition:
$TiO_2$(145 nm)/$SiO_2$(200 nm)/$TiO_2$(145 nm)/$SiO_2$(200 nm)/ $TiO_2$ (145 nm/$SiO_2$(200 nm)/$TiO_2$(145 nm)
100 g of $SiO_2$ flakes having a mean layer thickness of 200 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (474 g of a 60% $TiCl_4$ solution dissolved in 474 g of demineralized water), during which the pH is kept constant by simultaneous dropwise addition of 32% sodium hydroxide solution. When the addition is complete, the mixture is stirred for a further 15 minutes.

The pH of the suspension is then set to 7.5 using 32% sodium hydroxide solution, and the mixture is stirred for a further 15 minutes.

A sodium water-glass solution (654 g of sodium water-glass solution comprising 27.0% of $SiO_2$ are dissolved in 654 g of demineralized water) is subsequently added dropwise, during which the pH is kept constant at 7.5 by simultaneous metering-in of 18% hydrochloric acid. When the addition is complete, the mixture is stirred for a further 30 minutes.

The pH of the suspension is then set to 2.2 using 18% hydrochloric acid, the mixture is stirred for a further 30 minutes, and 949 g of a 30% titanium tetrachloride solution (preparation see above) are added dropwise. During this addition, the pH is kept constant at 2.2 by dropwise addition of 32% sodium hydroxide solution. The mixture is then stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 2:
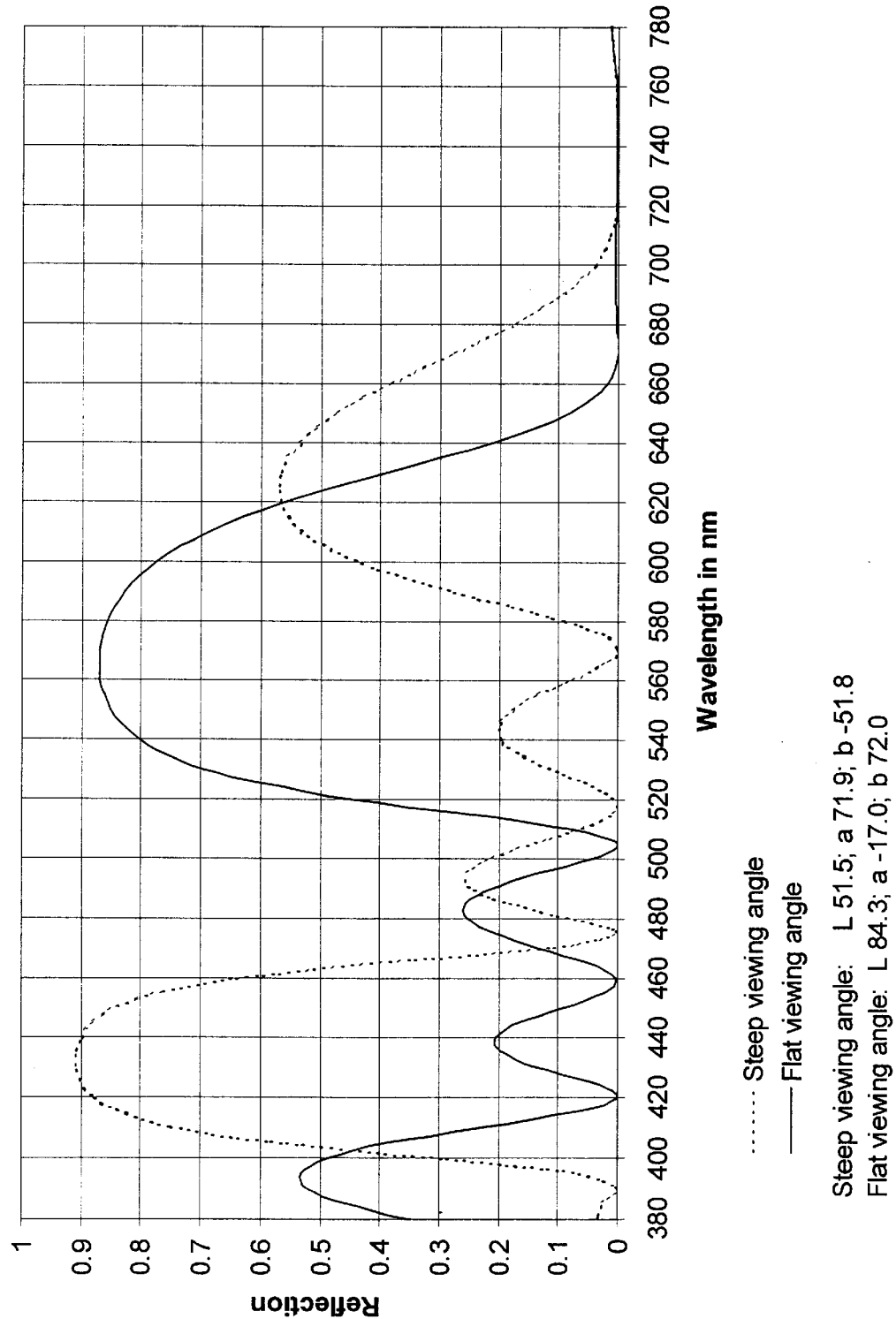

The corresponding Hunter L,a,b color diagram is shown with a dashed line in FIG. 1. It exhibits a color flop from violet to green-gold from a steep to flat viewing angle. The reflection spectrum (reflection as a function of the wavelength of visible light) is shown in FIG. 2.

Comparative Example 1

Preparation of a pigment having the composition
$TiO_2$(145 nm)/$SiO_2$(200 nm)/$TiO_2$(145 nm)
100 g of $SiO_2$ flakes having a mean layer thickness of 200 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (474 g of a 60% $TiCl_4$ solution dissolved in 474 g of demineralized water), during which the pH is kept constant by simultaneous dropwise addition of 32% sodium hydroxide solution. When the addition is complete, the mixture is stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 3:
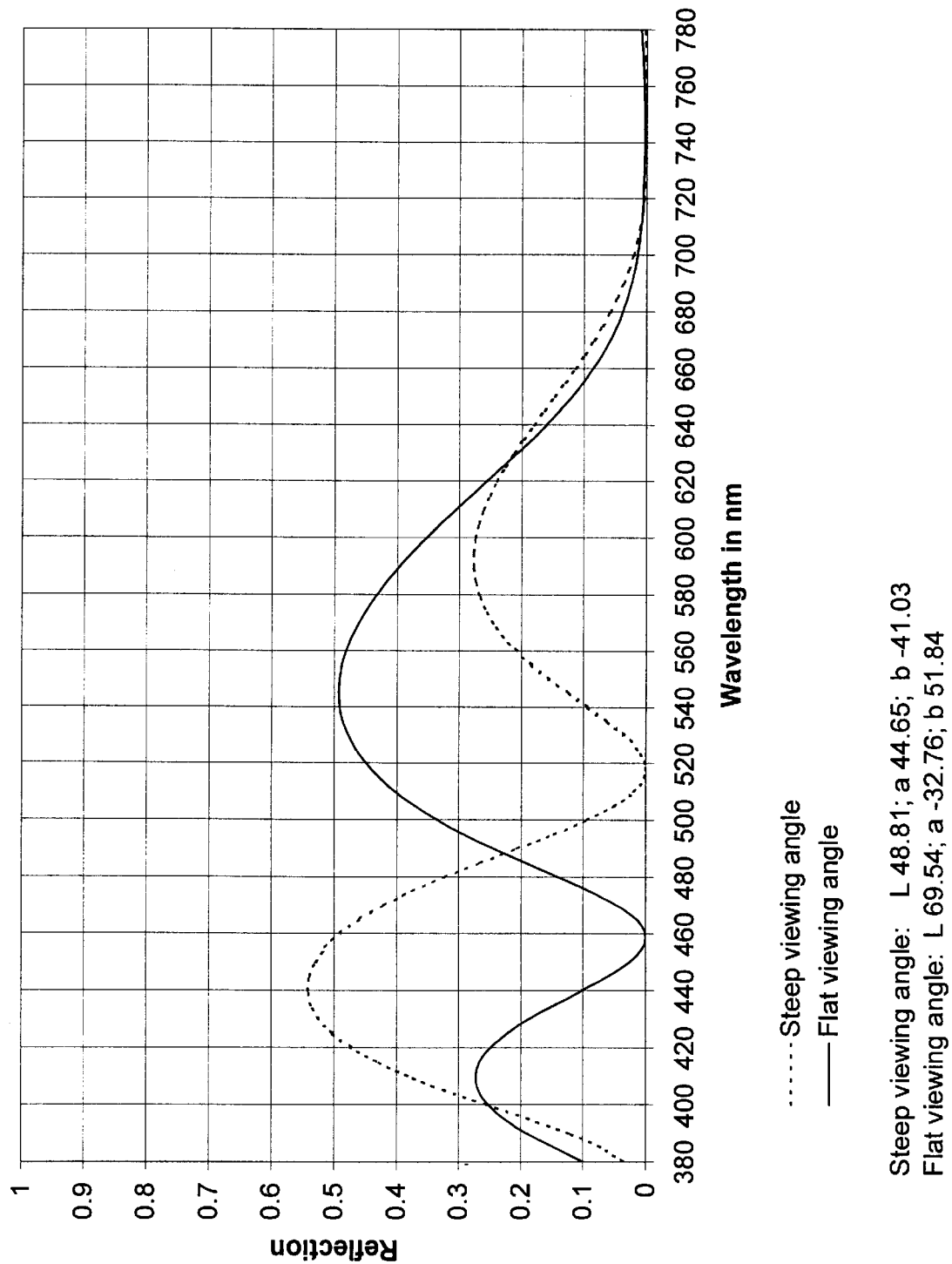

The Hunter L,a,b color diagram for Comparative Example 1 is shown with a continuous line in FIG. 1. It likewise exhibits a color flop from violet to green-gold from a steep to flat viewing angle. The reflection spectrum is shown in FIG. 3.

A comparison of the two reflection spectra of the pigments from Example 1 and Comparative Example 1 shows that the pigment in accordance with Example 1 of the present invention has a significantly improved reflection capacity compared with a three-layer pigment of comparable composition.

Example 2

Preparation of a pigment having the composition:
$TiO_2$(38 nm)/$SiO_2$(500 nm)/$TiO_2$(28 nm)/$SiO_2$(500 nm)/$TiO_2$(28 nm)/$SiO_2$(500 nm)/$TiO_2$(38 nm)
100 g of $SiO_2$ flakes having a mean layer thickness of 500 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (91.6 g of a 60% $TiCl_4$ solution dissolved in 91.6 g of demineralized water), during which the pH is kept constant by simultaneous dropwise addition of 32% sodium hydroxide solution. When the addition is complete, the mixture is stirred for a further 15 minutes.

The pH of the suspension is then set to 7.5 using 32% sodium hydroxide solution, and the mixture is stirred for a further 15 minutes.

A sodium water-glass solution (965 g of sodium water-glass solution comprising 27.0% of $SiO_2$ are dissolved in 965 g of demineralized water) is subsequently added dropwise, during which the pH is kept constant at 7.5 by simultaneous metering-in of 18% hydrochloric acid. When the addition is complete, the mixture is stirred for a further 30 minutes.

The pH of the suspension is then set to 2.2 using 18% hydrochloric acid, the mixture is stirred for a further 30 minutes, and 249 g of a 30% titanium tetrachloride solution (preparation see above) are added dropwise. During this addition, the pH is kept constant at 2.2 by dropwise addition of 32% sodium hydroxide solution. The mixture is then stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 4:
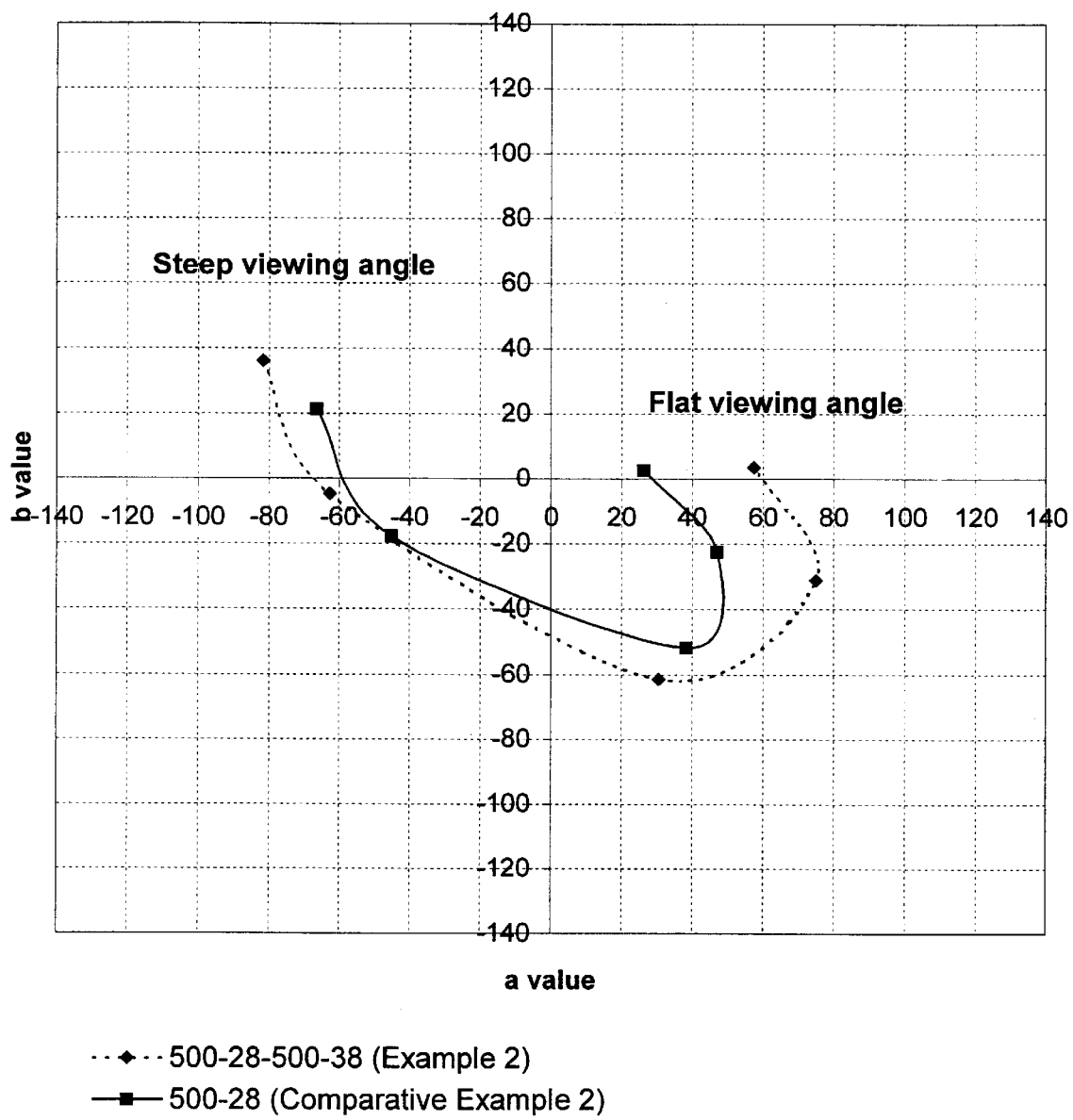
Figure 5:
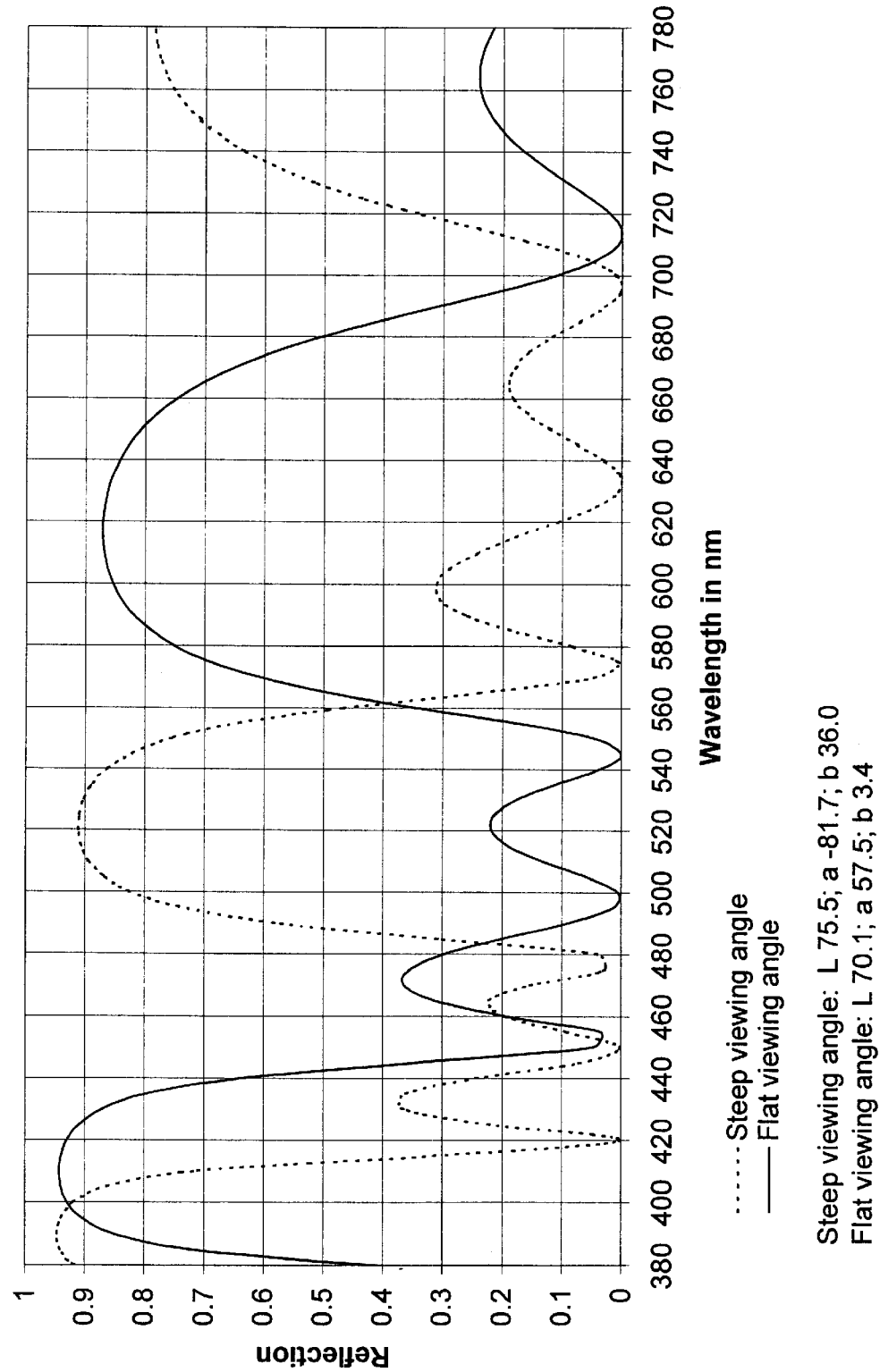

The L,a,b diagram obtained (see FIG. 4, dashed line) exhibits a color flop from green-gold at steep viewing angles to red at flat viewing angles. The reflection spectrum is shown in FIG. 5.

Comparative Example 2

Preparation of a pigment having the composition
$TiO_2$(28 nm)/$SiO_2$(500 nm)/$TiO_2$(28 nm)
100 g of $SiO_2$ flakes having a mean layer thickness of 500 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (91.6 g of a 60% $TiCl_4$ solution dissolved in 91.6 g of demineralized water), during which the pH is kept constant by simultaneous dropwise addition of 32% sodium hydroxide solution. When the addition is complete, the mixture is stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 6:
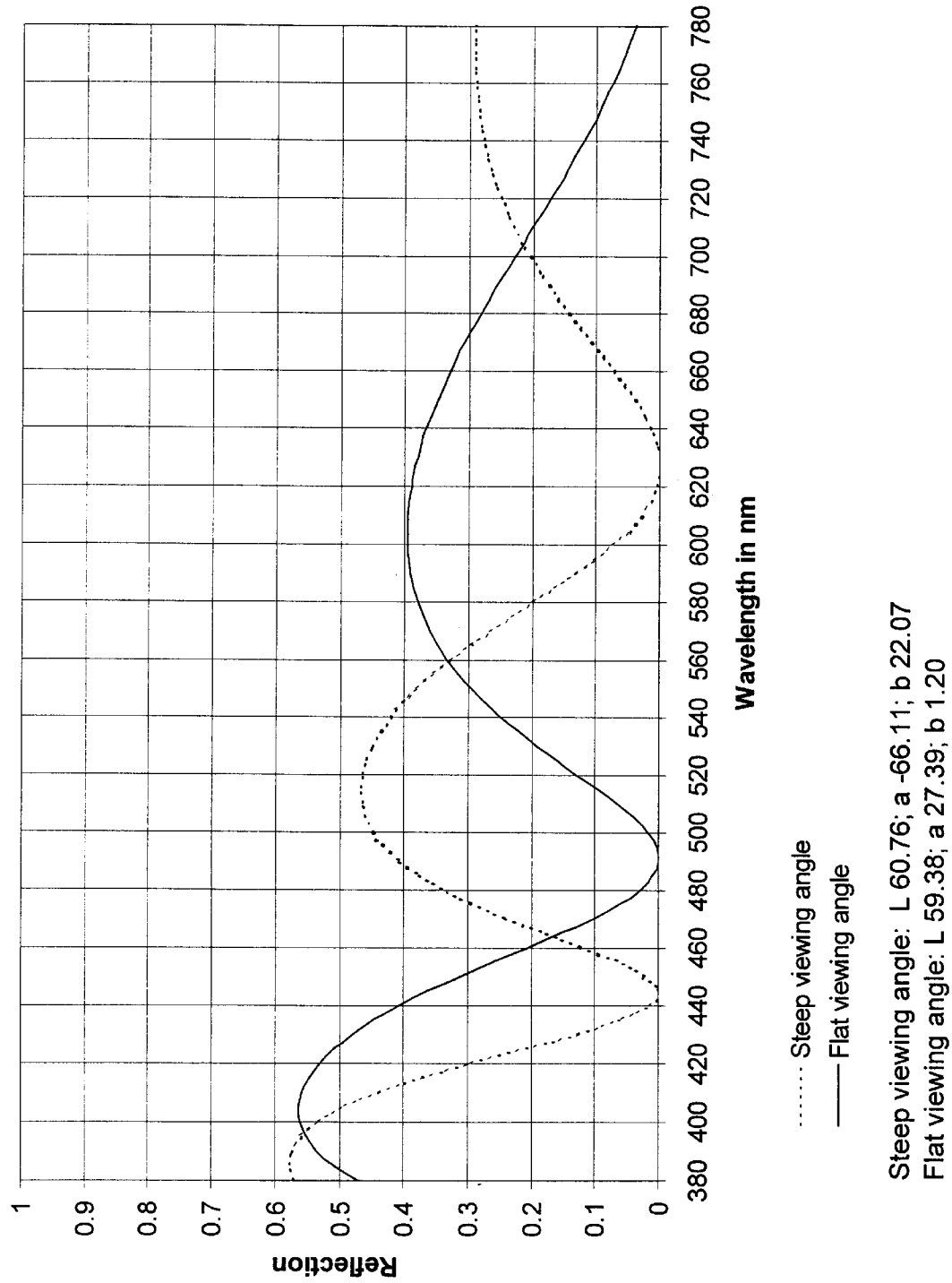

The L,a,b diagram obtained (see FIG. 4, continuous line) exhibits, as in Example 2, a color flop from green-gold at steep viewing angles to red at flat viewing angles. The reflection spectrum is shown in FIG. 6.

A comparison of the reflection spectra of Example 2 and Comparative Example 2 shows a significantly improved reflection capacity of the pigment in accordance with Example 2.

Example 3

Preparation of a pigment having the composition:
$TiO_2$(125 nm)/$SiO_2$(300 nm)/$TiO_2$(138 nm)/$SiO_2$(300 nm)/$TiO_2$(138 nm)/$SiO_2$(300 nm)/$TiO_2$(125 nm)

100 g of $SiO_2$ flakes having a mean layer thickness of 300 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (452 g of a 60% $TiCl_4$ solution dissolved in 452 g of demineralized water), during which the pH is kept constant by simultaneous dropwise addition of 32% sodium hydroxide solution. When the addition is complete, the mixture is stirred for a further 15 minutes.

The pH of the suspension is then set to 7.5 using 32% sodium hydroxide solution, and the mixture is stirred for a further 15 minutes.

A sodium water-glass solution (579 g of sodium water-glass solution comprising 27.3% of $SiO_2$ are dissolved in 579 g of demineralized water) is subsequently added dropwise, during which the pH is kept constant at 7.5 by simultaneous metering-in of 18% hydrochloric acid. When the addition is complete, the mixture is stirred for a further 30 minutes.

The pH of the suspension is then set to 2.2 using 18% hydrochloric acid, the mixture is stirred for a further 30 minutes, and 818 g of a 30% titanium tetrachloride solution (preparation see above) are added dropwise. During this addition, the pH is kept constant at 2.2 by dropwise addition of 32% sodium hydroxide solution. The mixture is then stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 7:
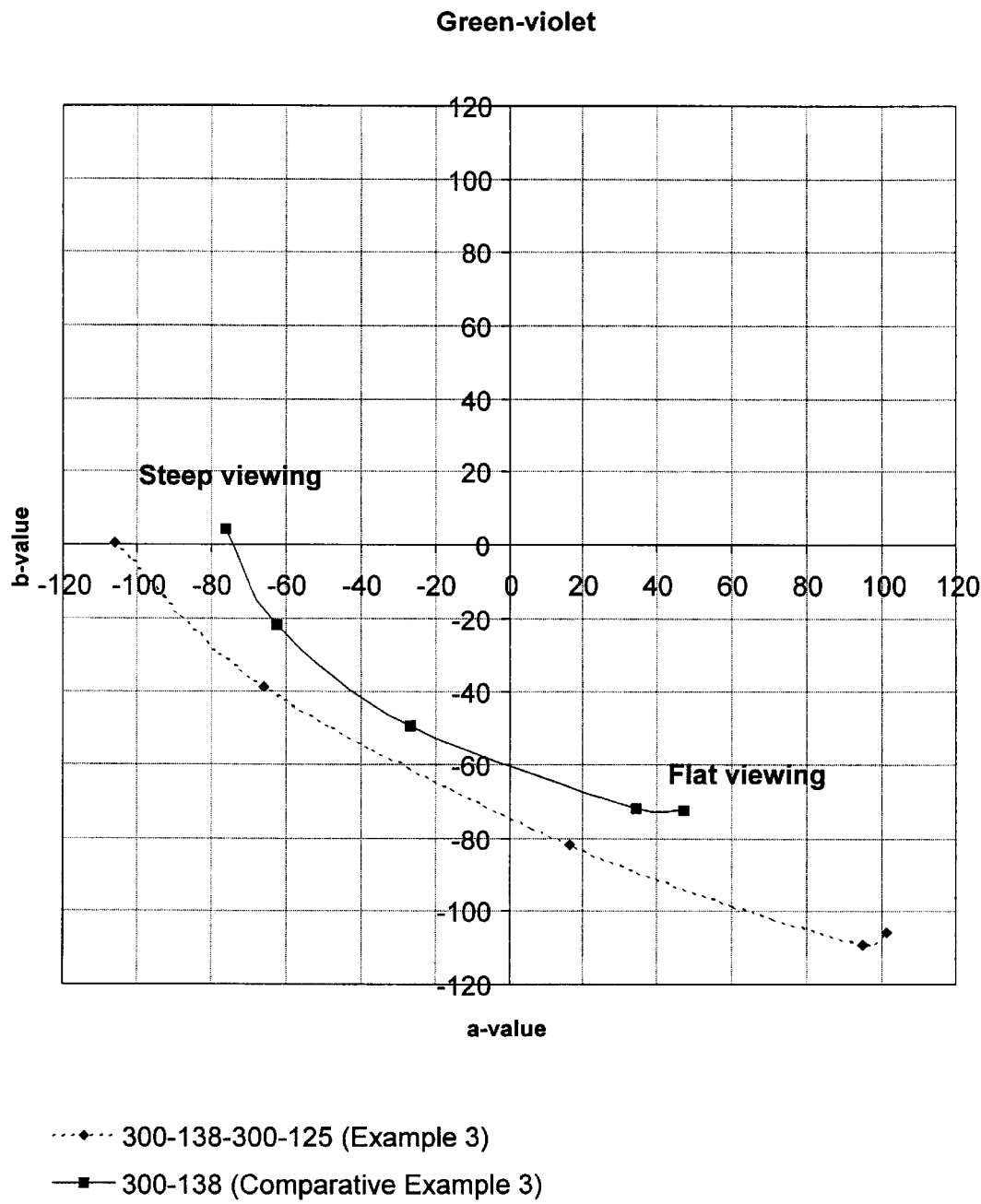
Figure 8:
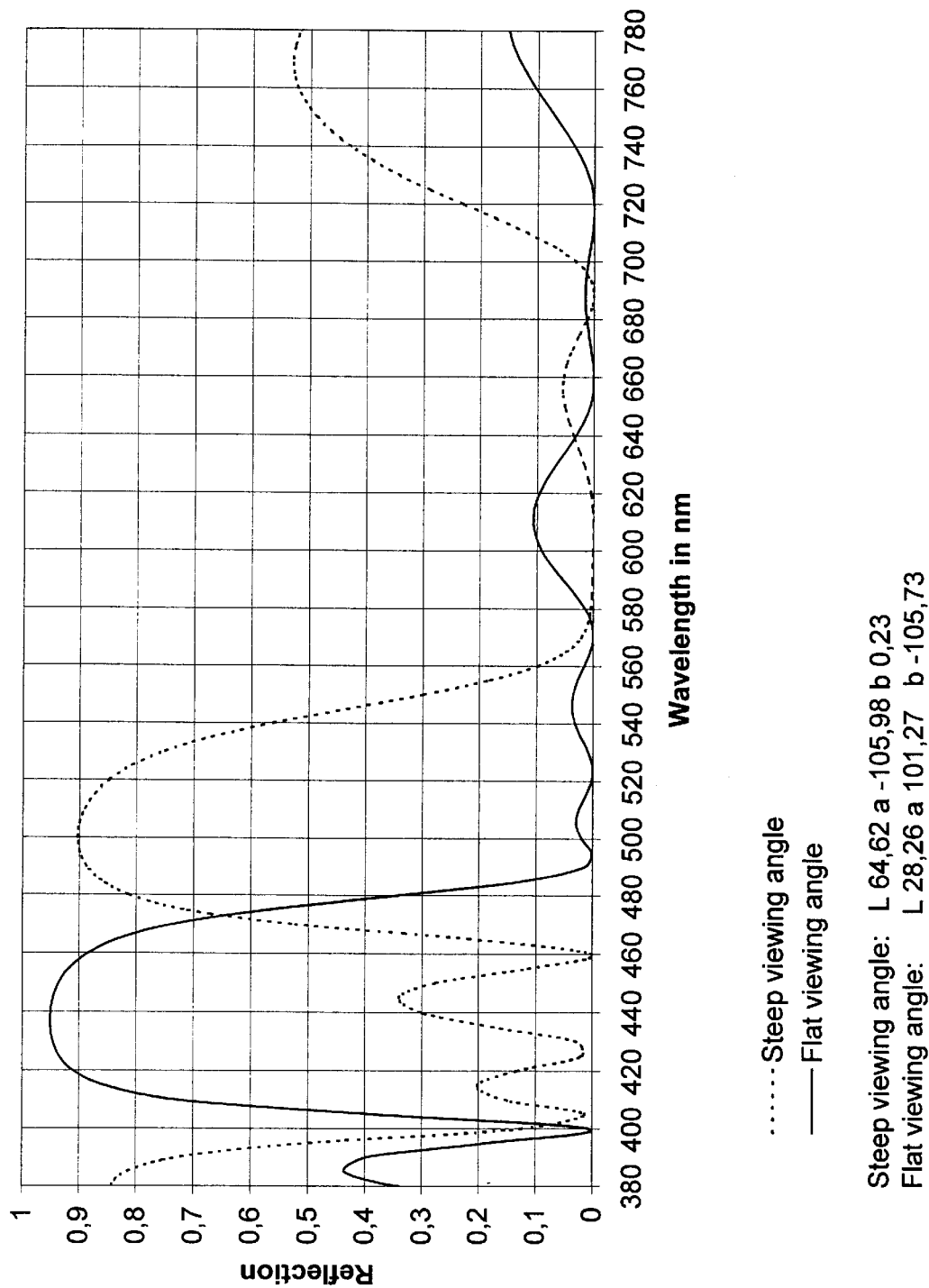

The L,a,b diagram obtained is shown with a dashed line in FIG. 7 and exhibits a color flop from green at steep viewing angles to violet at flat viewing angles. The corresponding reflection spectrum is shown in FIG. 8.

Comparative Example 3

Preparation of a pigment having the composition:
$TiO_2$(138 nm)/$SiO_2$(300 nm)/$TiO_2$(138 nm)

100 g of $SiO_2$ flakes having a mean layer thickness of 300 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (452 g of a 60% $TiCl_4$ solution dissolved in 452 g of demineralized water), during which the pH is kept constant by simultaneous dropwise addition of 32% sodium hydroxide solution. When the addition is complete, the mixture is stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

The L,a,b diagram obtained is shown with a continuous line in FIG. 7 and likewise exhibits a color flop from green at steep viewing angles to violet at flat viewing angles. The corresponding reflection spectrum is shown in FIG. 9.

Figure 9:
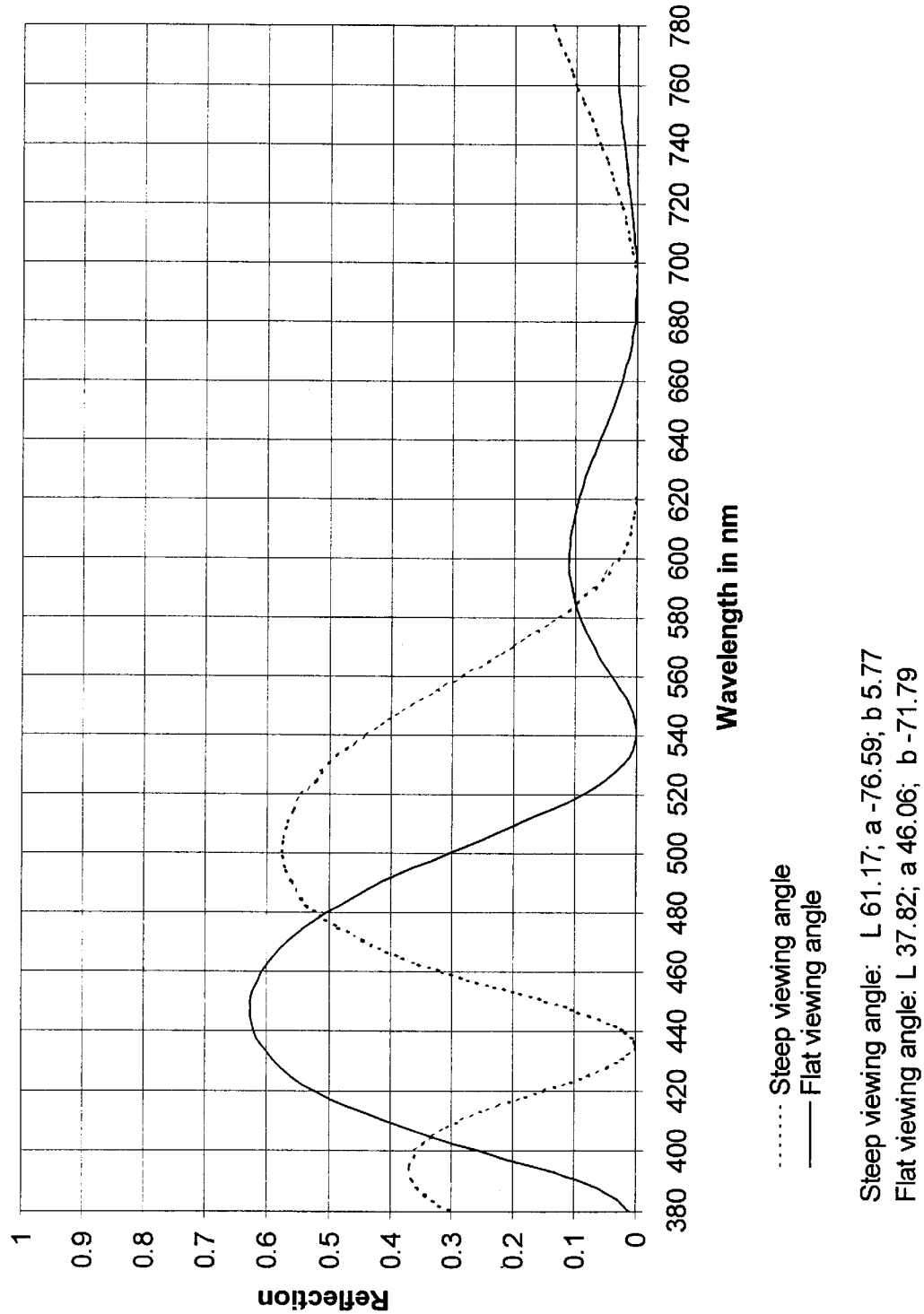

A comparison of the reflection spectra of FIGS. 8 and 9 shows that the pigment according to Example 3 has a significantly improved reflection capacity compared with Comparative Example 3.

Example 4

Preparation of a pigment having the composition:
$TiO_2$(73 nm)/$SiO_2$(300 nm)/$TiO_2$(70 nm)/$SiO_2$(300 nm)/$TiO_2$(70 nm)/$SiO_2$(300 nm)/$TiO_2$(73 nm)

100 g of $SiO_2$ flakes having a mean layer thickness of 300 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (229 g of a 60% $TiCl_4$ solution dissolved in 229 g of demineralized water), during which the pH is kept constant by simultaneous dropwise addition of 32% sodium hydroxide solution. When the addition is complete, the mixture is stirred for a further 15 minutes.

The pH of the suspension is then set to 7.5 using 32% sodium hydroxide solution, and the mixture is stirred for a further 15 minutes.

A sodium water-glass solution (579 g of sodium water-glass solution comprising 27.0% of $SiO_2$ are dissolved in 579 g of demineralized water) is subsequently added dropwise, during which the pH is kept constant at 7.5 by simultaneous metering-in of 18% hydrochloric acid. When the addition is complete, the mixture is stirred for a further 30 minutes.

The pH of the suspension is then set to 2.2 using 18% hydrochloric acid, the mixture is stirred for a further 30 minutes, and 478 g of a 30% titanium tetrachloride solution (preparation see above) are added dropwise. During this addition, the pH is kept constant at 2.2 by dropwise addition of 32% sodium hydroxide solution. The mixture is then stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 10:
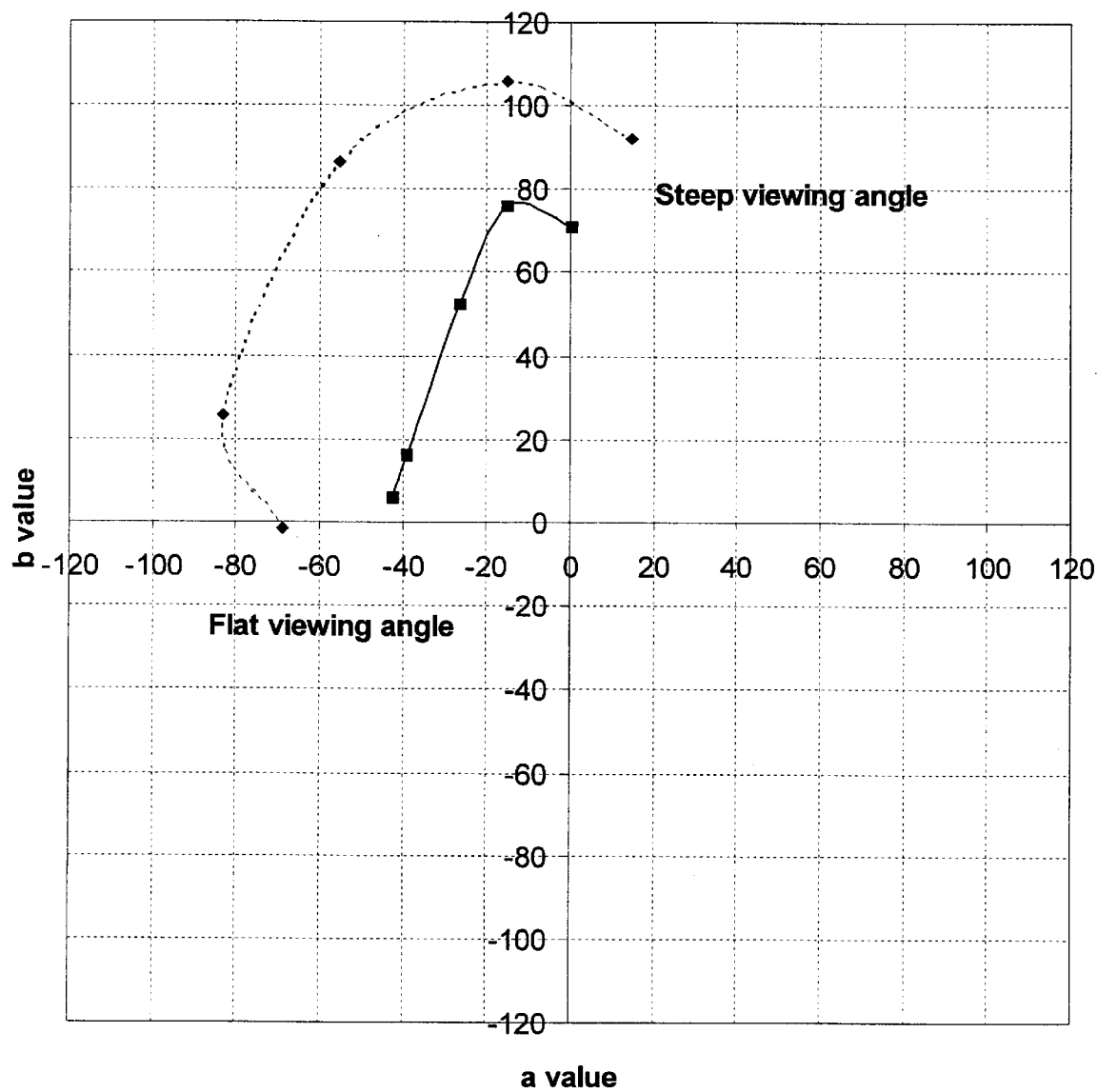
Figure 11:
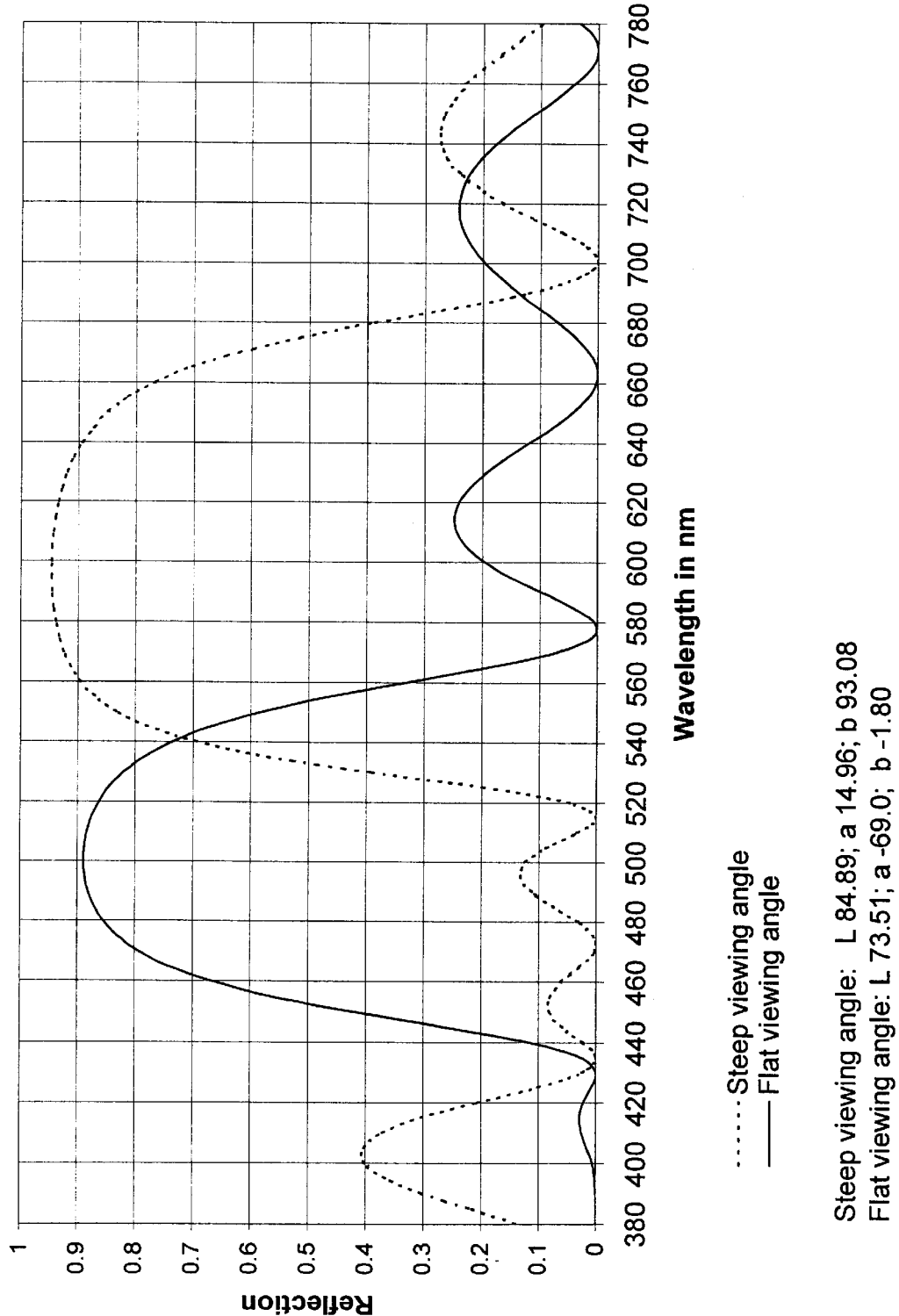

The L,a,b diagram obtained (see FIG. 10, dashed line) exhibits a color flop from gold at steep viewing angles to green at flat viewing angles. The reflection spectrum is shown in FIG. 11.

Comparative Example 4

Preparation of a pigment having the composition:
$TiO_2$(70 nm)/$SiO_2$(300 nm)/$TiO_2$(70 nm)

100 g of $SiO_2$ flakes having a mean layer thickness of 300 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (229 g of a 60% $TiCl_4$ solution dissolved in 229 g of demineralized water), during which the pH is kept constant by simultaneous dropwise addition of 32% sodium hydroxide solution. When the addition is complete, the mixture is stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 12:
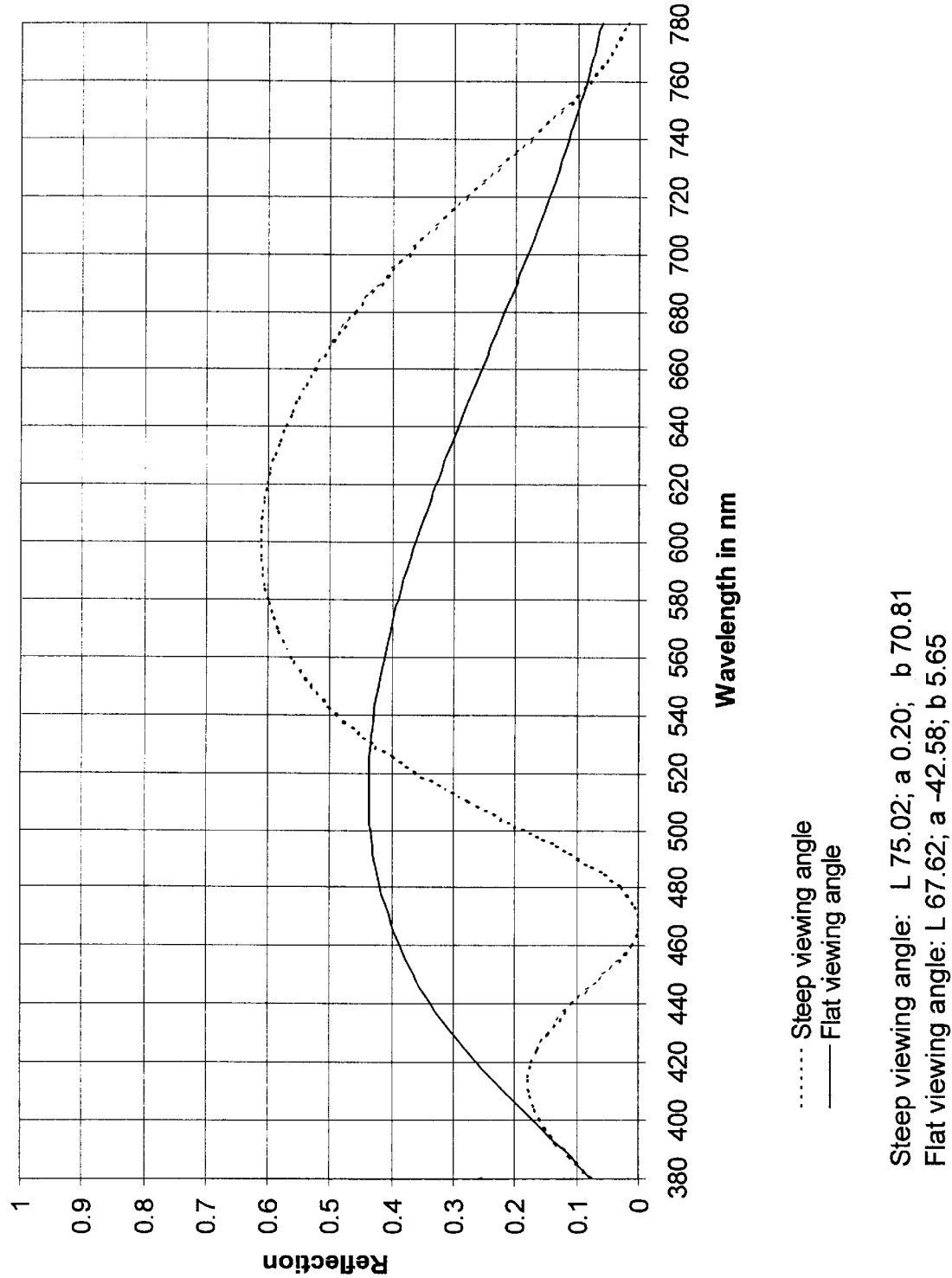

The L,a,b diagram obtained (see FIG. 10, continuous line) exhibits, as in Example 4, a color flop from gold at steep viewing angles to green at flat viewing angles. The reflection spectrum is shown in FIG. 12.

A comparison of the reflection spectra of the pigment in accordance with Example 4 and of the pigment in accordance with Comparative Example 4 shows a significantly better reflection capacity for the example according to the invention.

Example 5

Preparation of a pigment having the composition:
$TiO_2$(73 nm)/$SiO_2$(375 nm)/$TiO_2$(55 nm)/$SiO_2$(375 nm)/
    $TiO_2$(55 nm)/$SiO_2$(375 nm)/$TiO_2$(73 nm)
100 g of $SiO_2$ flakes having a mean layer thickness of 375 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (180 g of a 60% $TiCl_4$ solution dissolved in 180 g of demineralized water), during which the pH is kept constant by simultaneous dropwise addition of 32% sodium hydroxide solution. When the addition is complete, the mixture is stirred for a further 15 minutes.

The pH of the suspension is then set to 7.5 using 32% sodium hydroxide solution, and the mixture is stirred for a further 15 minutes.

A sodium water-glass solution (724 g of sodium water-glass solution comprising 27.0% of $SiO_2$ are dissolved in 724 g of demineralized water) is subsequently added dropwise, during which the pH is kept constant at 7.5 by simultaneous metering-in of 18% hydrochloric acid. When the addition is complete, the mixture is stirred for a further 30 minutes.

The pH of the suspension is then set to 2.2 using 18% hydrochloric acid, the mixture is stirred for a further 30 minutes, and 478 g of a 30% titanium tetrachloride solution (preparation see above) are added dropwise. During this addition, the pH is kept constant at 2.2 by dropwise addition of 32% sodium hydroxide solution. The mixture is then stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 13:
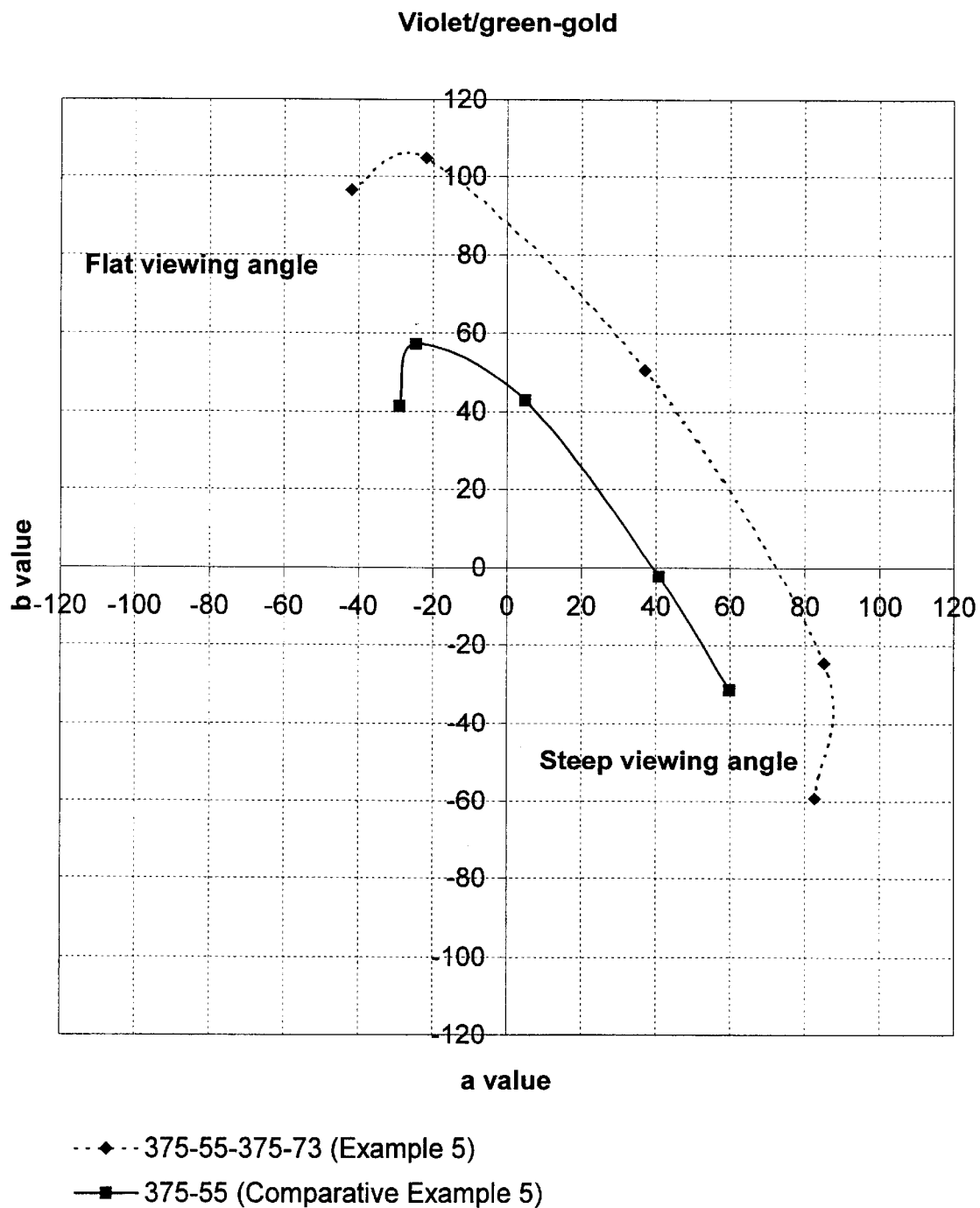

The L,a,b diagram obtained is shown with a dashed line in FIG. 13 and exhibits a color flop from violet at steep viewing angles to green-gold at flat viewing angles.

Figure 14:
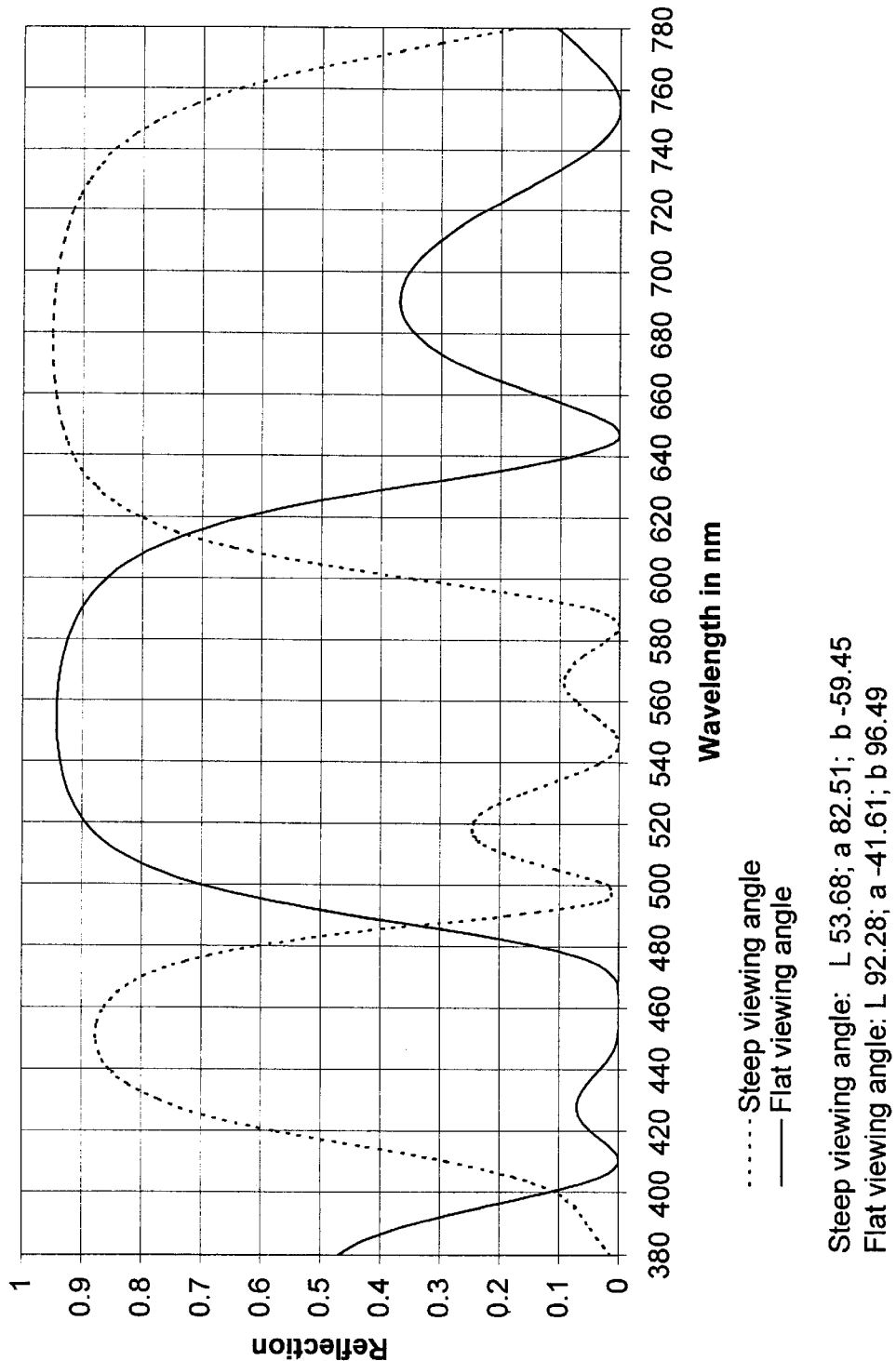

The corresponding reflection spectrum is shown in FIG. 14.

Comparative Example 5

Preparation of a pigment having the composition:
$TiO_2$(55 nm)/$SiO_2$(375 nm)/$TiO_2$(55 nm)
100 g of $SiO_2$ flakes having a mean layer thickness of 375 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (180 g of a 60% $TiCl_4$ solution dissolved in 180 g of demineralized water), during which the pH is kept constant by simultaneous dropwise addition of 32% sodium hydroxide solution. When the addition is complete, the mixture is stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

The L,a,b diagram obtained is shown with a continuous line in FIG. 13 and likewise exhibits a color flop from violet at steep viewing angles to green-gold at flat viewing angles. The corresponding reflection spectrum is shown in FIG. 15.

Figure 15:
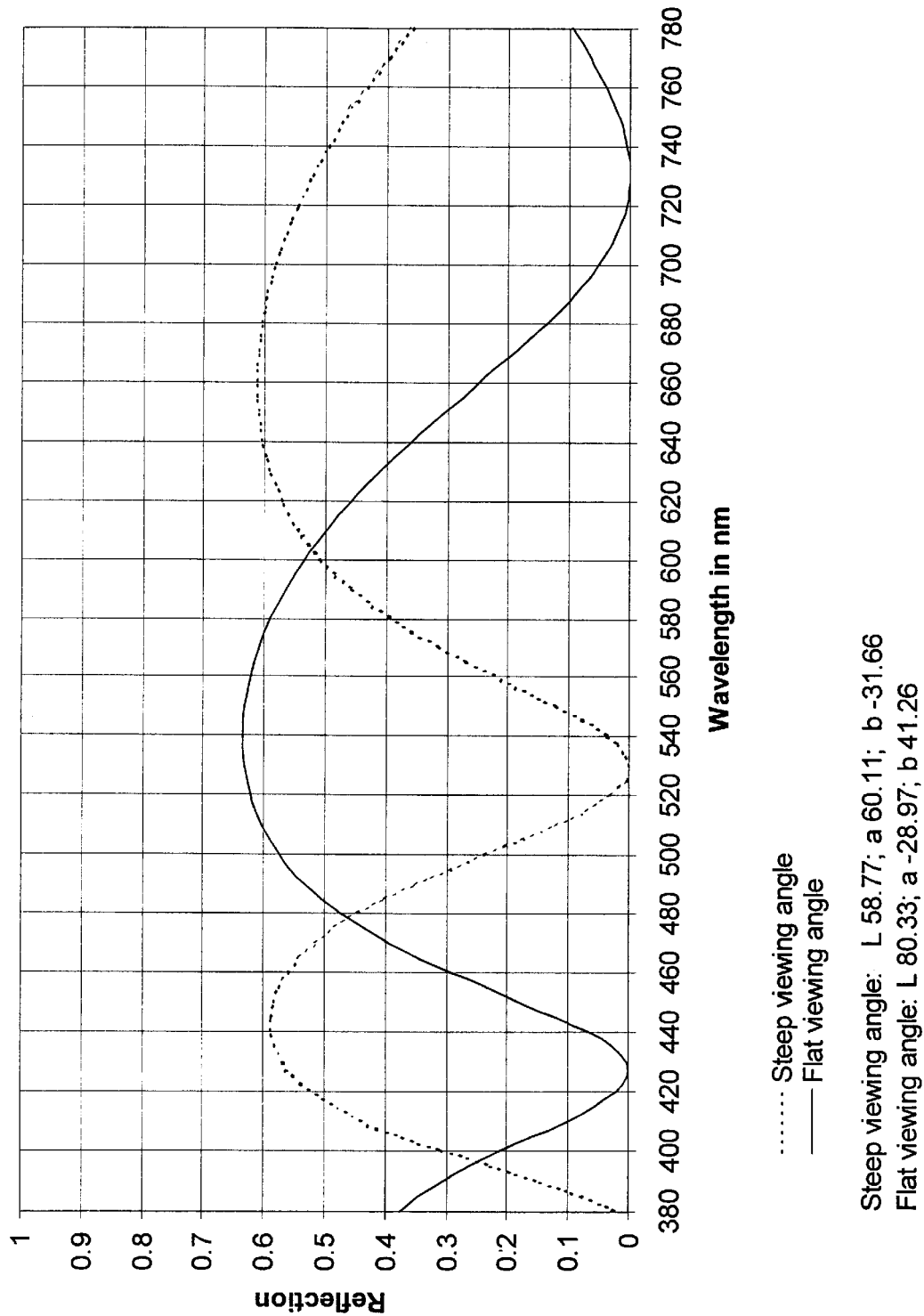

A comparison of the reflection spectra of FIGS. 14 and 15 shows that the pigment according to Example 5 has a significantly improved reflection capacity compared with Comparative Example 5.

Example 6

Preparation of a pigment having the composition:
$TiO_2$(48 nm)/$SiO_2$(280 nm)/$TiO_2$(48 nm)/$SiO_2$(280 nm)/
    $TiO_2$(48 nm)/$SiO_2$(280 nm)/$TiO_2$(48 nm)
100 g of $SiO_2$ flakes having a mean layer thickness of 280 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (157 g of a 60% $TiCl_4$ solution dissolved in 157 g of demineralized water), during which the pH is kept constant by simultaneous dropwise addition of 32% sodium hydroxide solution. When the addition is complete, the mixture is stirred for a further 15 minutes.

The pH of the suspension is then set to 7.5 using 32% sodium hydroxide solution, and the mixture is stirred for a further 15 minutes.

A sodium water-glass solution (540 g of sodium water-glass solution comprising 27.0% of $SiO_2$ are dissolved in 540 g of demineralized water) is subsequently added dropwise, during which the pH is kept constant at 7.5 by simultaneous metering-in of 18% hydrochloric acid. When the addition is complete, the mixture is stirred for a further 30 minutes.

The pH of the suspension is then set to 2.2 using 18% hydrochloric acid, the mixture is stirred for a further 30 minutes, and 314 g of a 30% titanium tetrachloride solution (preparation see above) are added dropwise. During this addition, the pH is kept constant at 2.2 by dropwise addition of 32% sodium hydroxide solution. The mixture is then stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 16:
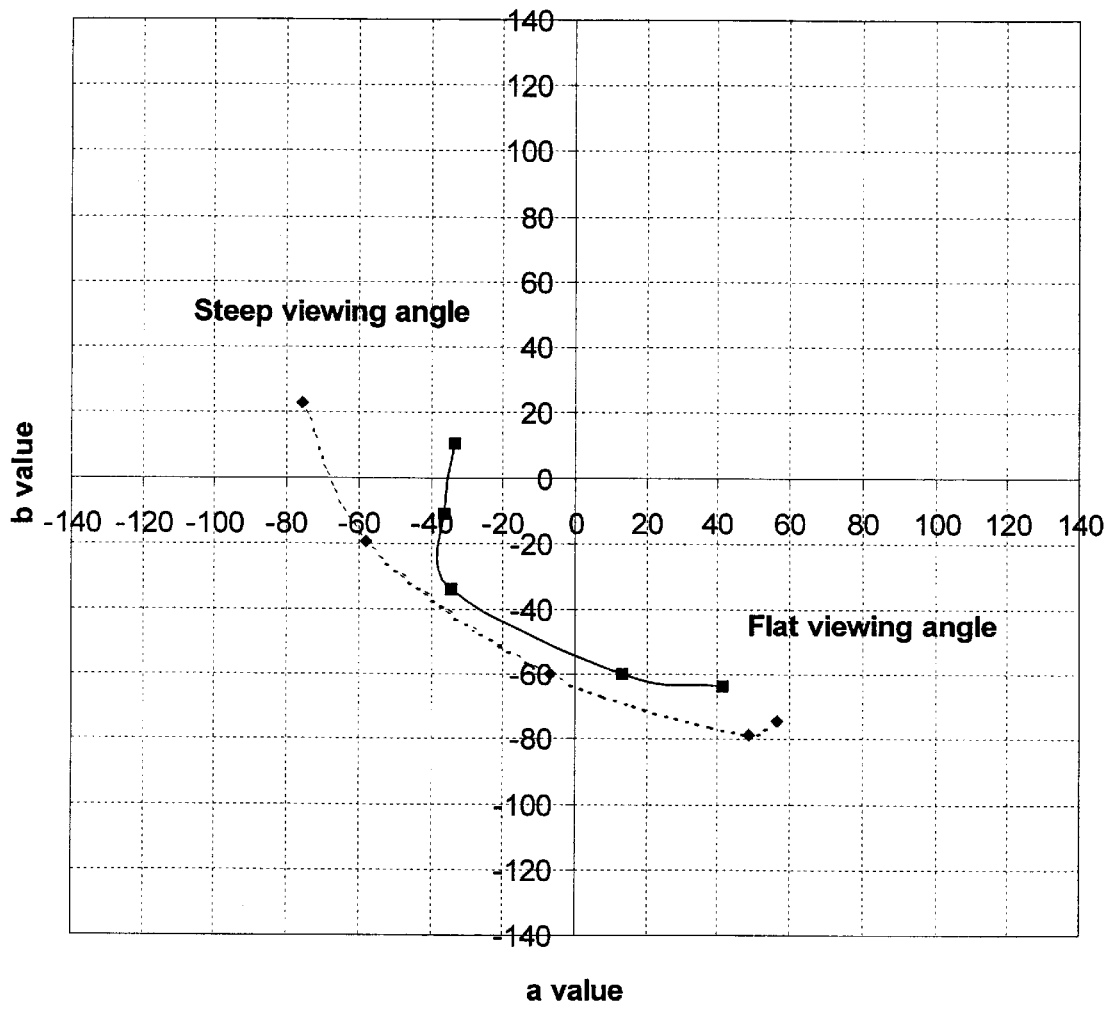
Figure 17:
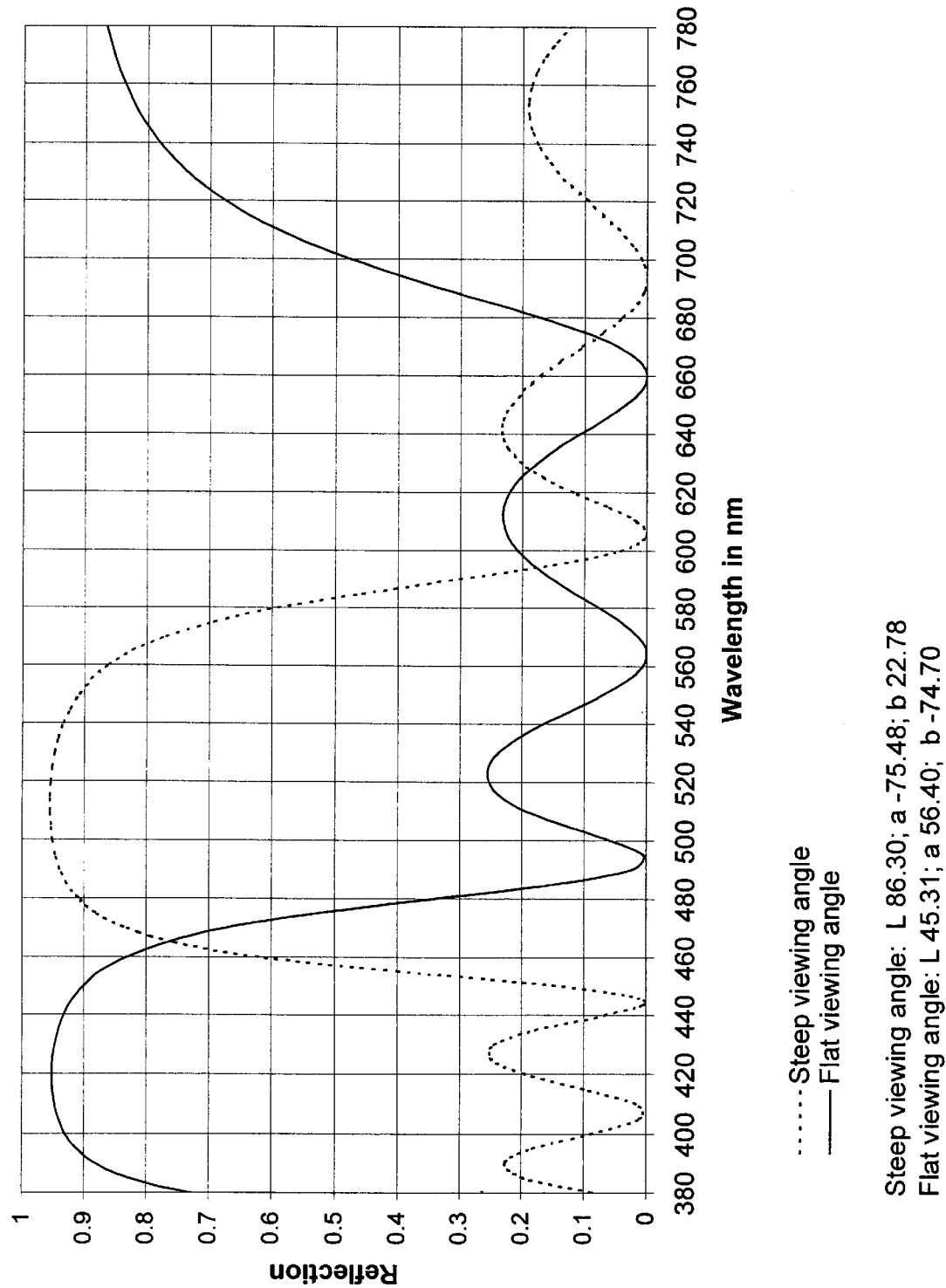

The L,a,b diagram obtained is shown with a dashed line in FIG. 16 and exhibits a color flop from green-gold at steep viewing angles via blue-green to violet at flat viewing angles. The chroma of the hues passed through is approximately equally pronounced. The reflection spectrum is shown in FIG. 17.

Comparative Example 6

Preparation of a pigment having the composition:
$TiO_2$(48 nm)/$SiO_2$(280 nm)/$TiO_2$(48 nm)
100 g of $SiO_2$ flakes having a mean layer thickness of 280 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (157 g of a 60% $TiCl_4$ solution dissolved in 157 g of demineralized water), during which the pH is kept constant by simultaneous dropwise addition of 32% sodium hydroxide solution. When the addition is complete, the mixture is stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

Figure 18:
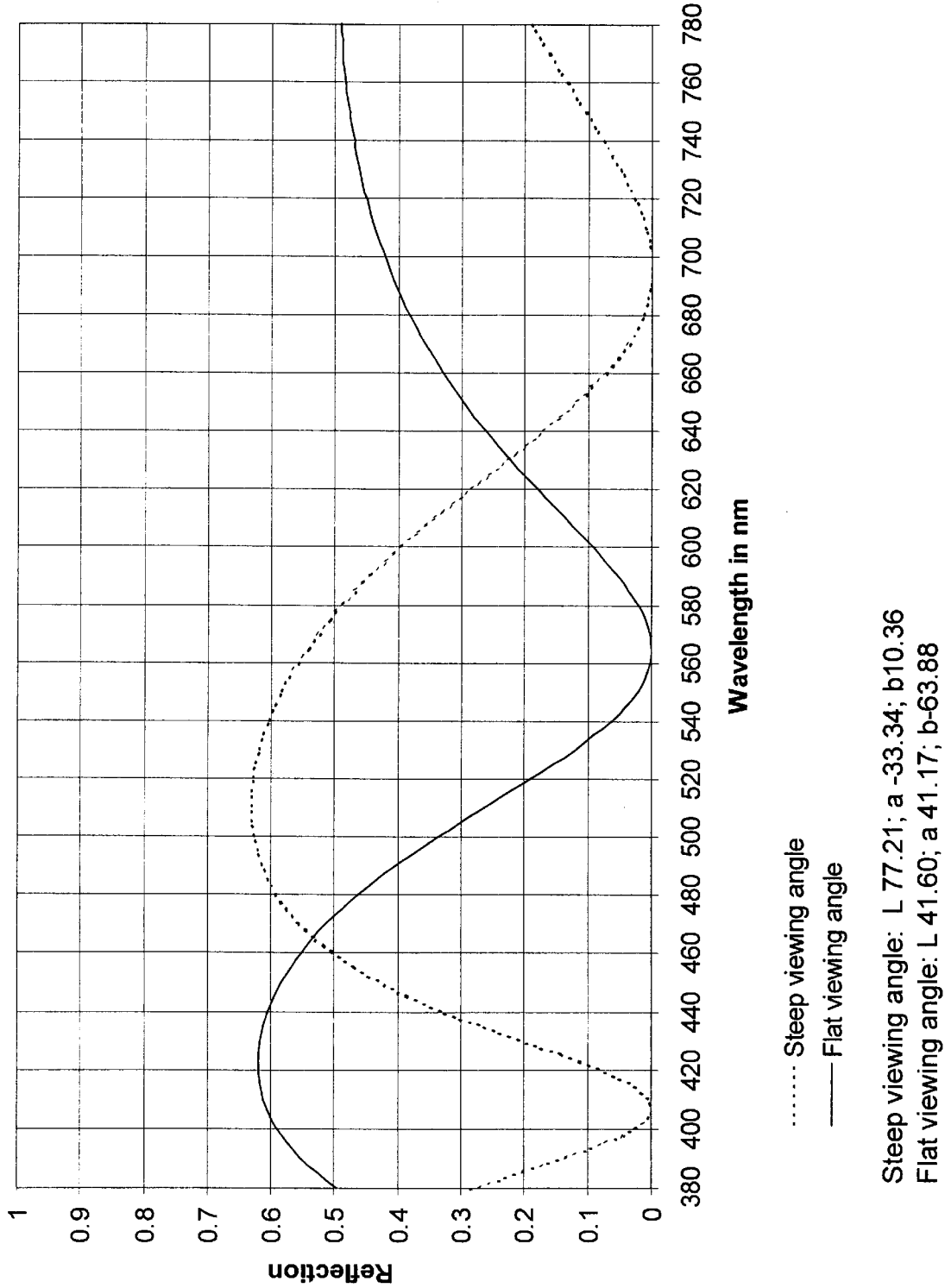

The L,a,b diagram obtained is shown with a continuous line in FIG. 16 and likewise exhibits a color flop from green-gold at steep viewing angles via blue-green to violet at flat viewing angles. The chroma of the hues passed through is differently pronounced and overall is weaker for each hue than in Example 6. The corresponding reflection spectrum is shown in FIG. 18.

A comparison of the reflection spectra of Example 6 and Comparative Example 6 shows a significantly better reflection capacity of the pigment in accordance with Example 6.

Comparative Example 7

Preparation of an asymmetrical pigment in accordance with Example 7 from DE 196 18 569, corresponds approximately to the pigment in accordance with Example 6, but with an asymmetrical structure:
$TiO_2$(48 nm)/$SiO_2$(173 nm)/$TiO_2$(33 nm)/$SiO_2$(280 nm)/ $TiO_2$(33 nm)/$SiO_2$(173 nm)/$TiO_2$(48 nm)
100 g of $SiO_2$ flakes having a mean layer thickness of 280 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (108 g of a 60% $TiCl_4$ solution dissolved in 108 g of demineralized water), during which the pH is kept constant by simultaneous dropwise addition of 32% sodium hydroxide solution. When the addition is complete, the mixture is stirred for a further 15 minutes.

The pH of the suspension is then set to 7.5 using 32% sodium hydroxide solution, and the mixture is stirred for a further 15 minutes.

A sodium water-glass solution (334 g of sodium water-glass solution comprising 27.0% of $SiO_2$ are dissolved in 334 g of demineralized water) is subsequently added dropwise, during which the pH is kept constant at 7.5 by simultaneous metering-in of 18% hydrochloric acid. When the addition is complete, the mixture is stirred for a further 30 minutes.

The pH of the suspension is then set to 2.2 using 18% hydrochloric acid, the mixture is stirred for a further 30 minutes, and 314 g of a 30% titanium tetrachloride solution (preparation see above) are added dropwise. During this addition, the pH is kept constant at 2.2 by dropwise addition of 32% sodium hydroxide solution. The mixture is then stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

The L,a,b diagram obtained (see FIG. 19, dashed line) exhibits a color flop from gold-green at steep viewing angles via blue-green to violet at flat viewing angles. However, the chroma is very different for the various colors and is only sufficiently intense in the gold-green region. The reflection spectrum is shown in FIG. 20.

Comparative Example 7'

Preparation of a pigment having the composition:
$TiO_2$(33 nm)/$SiO_2$(280 nm)/$TiO_2$(33 nm)
100 g of $SiO_2$ flakes having a mean layer thickness of 280 nm are suspended in 1.9 l of demineralized water with stirring and heated to 75° C.

The pH of the suspension is then adjusted to 2.2 using 18% hydrochloric acid. This is followed by metering-in of a 30% titanium tetrachloride solution (108 g of a 60% $TiCl_4$ solution dissolved in 108 g of demineralized water), during which the pH is kept constant by simultaneous dropwise addition of 32% sodium hydroxide solution. When the addition is complete, the mixture is stirred for a further 15 minutes.

The product is filtered off, washed, dried, calcined at 800° C. and sieved through a 100 μm sieve, and paint cards of the pigment are prepared after incorporation into nitrocellulose lacquer and these are measured coloristically.

The L,a,b diagram obtained (see FIG. 19, continuous line) exhibits a color flop from blue-green at steep viewing angles to violet at flat viewing angles. The reflection spectrum is shown in FIG. 21.

Figure 20:
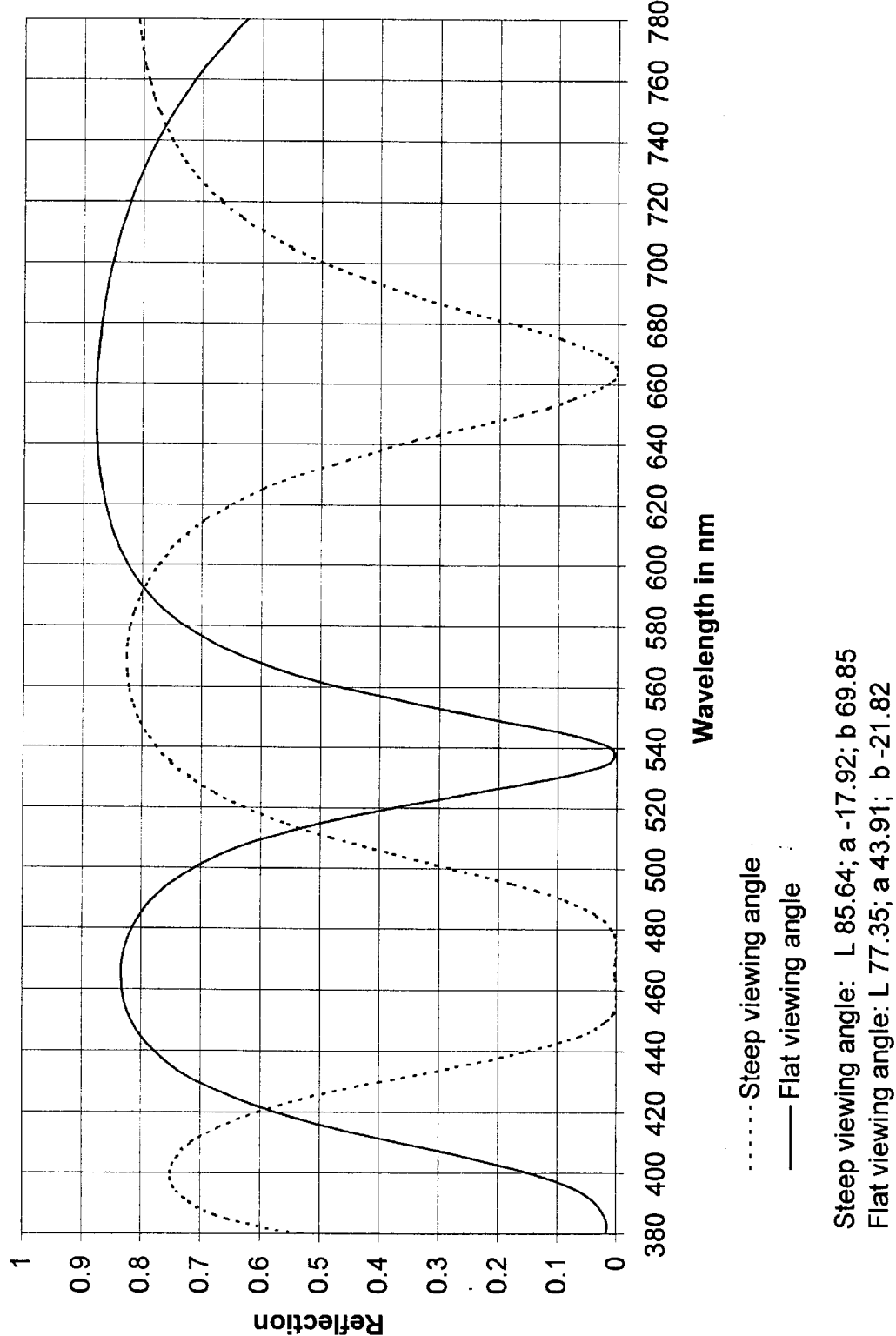
Figure 21:
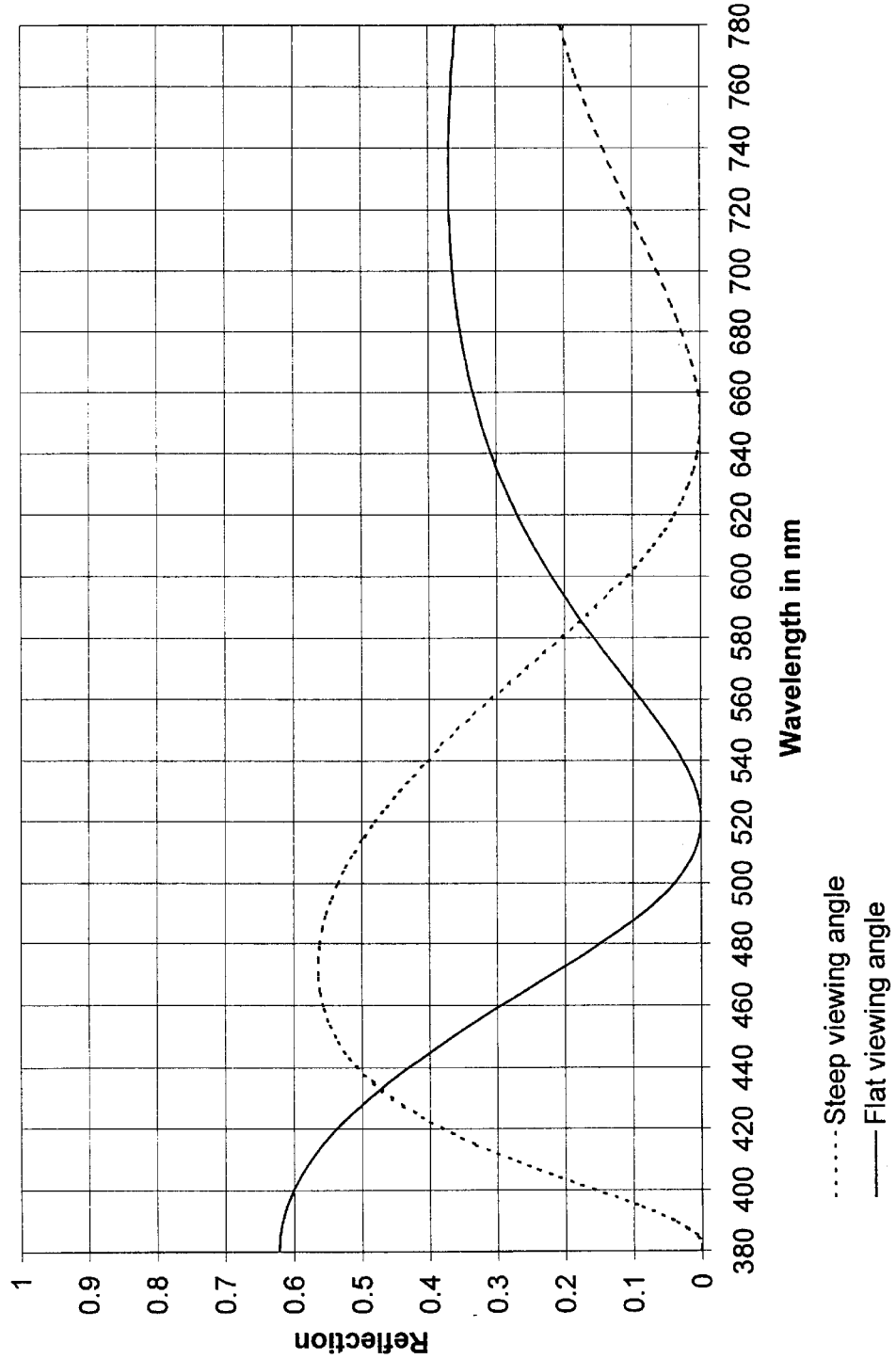

The comparison of the reflection spectra of FIGS. 20 and 21 shows an improved reflection capacity of the pigment in accordance with Comparative Example 7.

Figure 19:
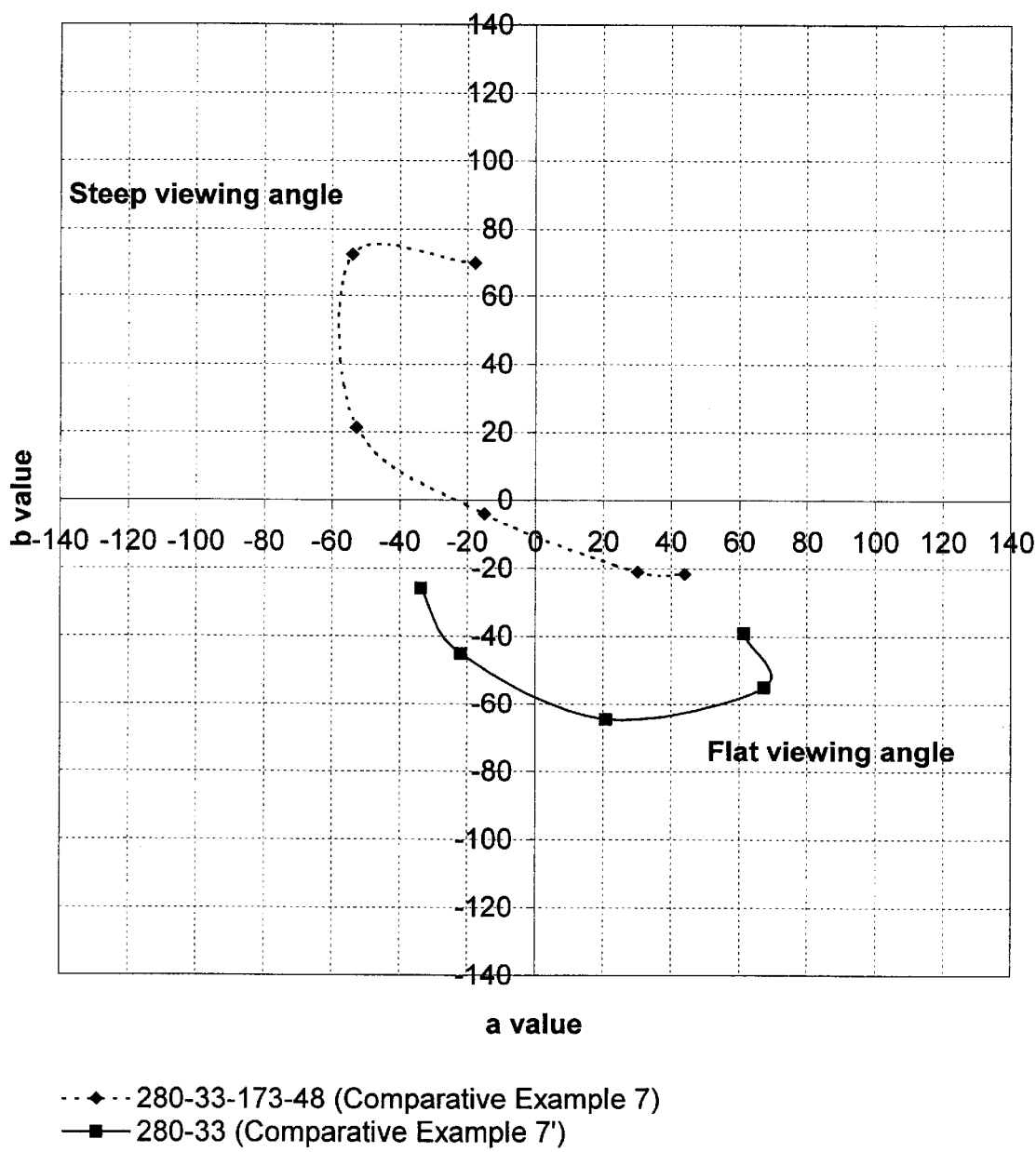

At the same time, however, the asymmetrical structure completely shifts the color-flop behaviour compared with the 3-layer system in accordance with Comparative Example 7' (see FIG. 19). Whereas the most intense color of the pigment in accordance with Comparative Example 7 is in the gold-green region, the gold-green hue is not present in Comparative Example 7' and the violet hue is the most pronounced.

The asymmetrical pigment in accordance with Comparative Example 7 thus exhibits a completely different color-flop behaviour compared with the comparable symmetrical pigment in accordance with Example 6, with the pigment in accordance with Example 6, in contrast to Comparative Example 7, additionally having equally good hues in all color regions passed through.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A multilayered interference pigment, comprising a substrate of platelet-shaped silicon dioxide which is coated alternately with two or more layers of light-transparent materials having refractive indices of n>1.8 and therebetween one or more layers of light-transparent materials having refractive indices of n≦1.8, where the optical thickness of the platelet-shaped substrate and the optical thickness of the individual layers of light-transparent materials having refractive indices of n≦1.8 is substantially the same.

2. A multilayered interference pigment, comprising a substrate of platelet-shaped silicon dioxide which is coated alternately with two or more layers of light-transparent materials having refractive indices of n>1.8 and therebetween one or more layers of light-transparent materials having refractive indices of n≦1.8, where the optical thickness of the platelet-shaped substrate and the optical thickness of the individual layers of light-transparent materials having refractive indices of n≦1.8 is the same.

3. A multilayered interference pigment according to claim 1, which is coated with two layers of light-transparent materials having refractive indices of n>1.8 and therebetween one layer of a light-transparent material having refractive index of n≦1.8.

4. A multilayered interference pigment according to claim 1, wherein the light-transparent materials having refractive indices of n>1.8 are $TiO_2$, $ZrO_2$, ZnO, $SnO_2$, a mixture thereof, or BiOCl.

5. A multilayered interference pigment according to claim 4, wherein at least one light-transparent material having a refractive index of n>1.8 is $TiO_2$.

6. A multilayered interference pigment according to claim 1, wherein the light-transparent materials having refractive indices of $n \leq 1.8$ are $SiO_2$, $SiO(OH)_2$, $Al_2O_3$, $AlOOH$, $B_2O_3$, $MgF_2$ or a mixture thereof.

7. A multilayered interference pigment according to claim 6, wherein the light-transparent material having a refractive index of $n \leq 1.8$ is $SiO_2$.

8. A multilayered interference pigment according to claim 1, wherein the platelet-shaped substrate and the individual layers of light-transparent materials having refractive indices of $n \leq 1.8$ each have layer thicknesses of between 100 and 600 nm.

9. A multilayered interference pigment according claim 1, wherein the layers of light-transparent materials having refractive indices of $n > 1.8$ each have layer thicknesses of between 20 and 300 nm.

10. A multilayered interference pigment according to claim 9, wherein the layer thicknesses of each layer of light-transparent material having refractive indices of $n > 1.8$ are the same.

11. A multilayered interference pigment according to claim 1, wherein each layer of light-transparent material having refractive indices of $n \leq 1.8$ has greater layer thicknesses than the layers of light-transparent materials having refractive indices of $n > 1.8$.

12. A process for the preparation of a multilayered pigment according to claim 1, comprising suspending a platelet-shaped substrate of silicon dioxide in water and coating alternately a number of times with a metal oxide hydrate or BiOCl having a refractive index of $n > 1.8$ and a metal oxide hydrate or metal fluoride having a refractive index of $n \leq 1.8$, by addition and precipitation of corresponding inorganic metal compounds.

13. A process according to claim 12, wherein pH necessary for precipitation of the respective metal oxide hydrate, BiOCl or metal fluoride is set and kept constant by simultaneous addition of acid or base, and a coated substrate is subsequently separated off from aqueous suspension, dried and, optionally calcined.

14. A process according to claim 13, wherein an optical layer thickness of individual layers of a metal oxide hydrate or metal fluoride having a refractive index of $n \leq 1.8$ to be applied to the substrate is selected so that it is equal to the optical layer thickness of the platelet-shaped substrate after drying and any calcination.

15. A paint, laquer, printing ink, plastic, cosmetic formulation, ceramic material, paper, film, packaging material, glass, pigment preparation, dry preparation, security application or laser marking substrate, comprising a multilayered pigment according claim 1.

* * * * *